(12) United States Patent
Juhasz et al.

(10) Patent No.: US 8,398,236 B2
(45) Date of Patent: Mar. 19, 2013

(54) IMAGE-GUIDED DOCKING FOR OPHTHALMIC SURGICAL SYSTEMS

(75) Inventors: Adam Juhasz, Costa Mesa, CA (US); Kostadin Vardin, Aliso Viejo, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 219 days.

(21) Appl. No.: 12/815,179

(22) Filed: Jun. 14, 2010

(65) Prior Publication Data

US 2011/0304819 A1 Dec. 15, 2011

(51) Int. Cl.
*A61B 3/14* (2006.01)
*A61B 3/00* (2006.01)

(52) U.S. Cl. .................... 351/206; 351/208; 351/246

(58) Field of Classification Search .......... 351/205–206, 351/200, 208–210, 221–223, 246
See application file for complete search history.

(56) References Cited

U.S. PATENT DOCUMENTS

| | | |
|---|---|---|
| 4,164,222 A | 8/1979 | Prokhorov et al. |
| 4,198,143 A | 4/1980 | Karasawa |
| 4,235,529 A | 11/1980 | Kawase et al. |
| 4,465,348 A | 8/1984 | Lang |
| 4,520,816 A | 6/1985 | Schachar et al. |
| 4,533,222 A | 8/1985 | Ishikawa |
| 4,538,608 A | 9/1985 | L'Esperance, Jr. |
| 4,554,917 A | 11/1985 | Tagnon |
| 4,638,801 A | 1/1987 | Daly et al. |
| 4,764,005 A * | 8/1988 | Webb et al. ............... 351/205 |
| 4,881,808 A | 11/1989 | Bille et al. |
| 4,901,718 A | 2/1990 | Bille et al. |
| 4,907,586 A | 3/1990 | Bille et al. |
| 5,048,946 A | 9/1991 | Sklar et al. |
| 5,049,147 A | 9/1991 | Danon |
| 5,054,907 A | 10/1991 | Sklar et al. |
| 5,098,426 A | 3/1992 | Sklar et al. |
| 5,139,022 A | 8/1992 | Lempert |
| 5,246,435 A | 9/1993 | Bille et al. |
| 5,255,025 A | 10/1993 | Volk |
| 5,286,964 A | 2/1994 | Fountain |
| 5,321,501 A | 6/1994 | Swanson et al. |

(Continued)

FOREIGN PATENT DOCUMENTS

| | | |
|---|---|---|
| EP | 1444946 A1 | 8/2004 |
| JP | 2002345758 | 12/2002 |

(Continued)

OTHER PUBLICATIONS

U.S. Appl. No. 90/006,816, filed Feb. 27, 2007, Swanson et al.

(Continued)

*Primary Examiner* — Dawayne A Pinkney

(57) ABSTRACT

A docking method for an ophthalmic system may include the steps of aligning a docking unit of the ophthalmic system and an eye; generating an image of an internal structure of the eye by an imaging system; improving an alignment of the docking unit with the internal structure of the eye in relation to the generated image; and docking the docking unit to the eye. The generating the image step may include computing scanning data by a processor corresponding to a scanning pattern; storing the scanning data in a data buffer; transferring the scanning data by the data buffer to an output module; outputting scanning signals by the output module to one or more scanners based on the scanning data; and scanning an imaging beam with the one or more scanners according to the scanning signals.

40 Claims, 12 Drawing Sheets

U.S. PATENT DOCUMENTS

| | | | |
|---|---|---|---|
| 5,336,215 A | 8/1994 | Hsueh et al. |
| 5,439,462 A | 8/1995 | Bille et al. |
| 5,493,109 A | 2/1996 | Wei et al. |
| 5,549,632 A | 8/1996 | Lai |
| 5,656,186 A | 8/1997 | Mourou et al. |
| 5,738,676 A | 4/1998 | Hammer et al. |
| 5,779,696 A | 7/1998 | Berry et al. |
| 5,795,295 A | 8/1998 | Hellmuth et al. |
| 5,936,706 A | 8/1999 | Takagi |
| 5,954,648 A | 9/1999 | Van Der Brug |
| 5,954,711 A | 9/1999 | Ozaki et al. |
| 5,994,690 A | 11/1999 | Kulkarni et al. |
| 6,004,314 A | 12/1999 | Wei et al. |
| 6,095,648 A | 8/2000 | Birngruber et al. |
| 6,099,522 A | 8/2000 | Knopp et al. |
| 6,137,585 A | 10/2000 | Hitzenberger et al. |
| 6,254,595 B1 | 7/2001 | Juhasz et al. |
| 6,288,784 B1 | 9/2001 | Hitzenberger et al. |
| 6,314,311 B1 | 11/2001 | Williams et al. |
| 6,317,616 B1 | 11/2001 | Glossop |
| 6,337,925 B1 | 1/2002 | Cohen et al. |
| 6,377,349 B1 | 4/2002 | Fercher |
| 6,379,005 B1 | 4/2002 | Williams et al. |
| 6,451,009 B1 | 9/2002 | Dasilva et al. |
| 6,454,761 B1 | 9/2002 | Freedman |
| 6,497,701 B2 | 12/2002 | Shimmick et al. |
| 6,529,758 B2 | 3/2003 | Shahidi |
| 6,579,282 B2 | 6/2003 | Bille et al. |
| 6,623,476 B2 | 9/2003 | Juhasz et al. |
| 6,687,010 B1 | 2/2004 | Horii et al. |
| 6,730,074 B2 | 5/2004 | Bille et al. |
| 6,741,359 B2 | 5/2004 | Wei et al. |
| 6,751,033 B2 | 6/2004 | Goldstein et al. |
| 6,755,819 B1 | 6/2004 | Waelti |
| 6,763,259 B1 | 7/2004 | Hauger et al. |
| 6,769,769 B2 | 8/2004 | Podoleanu et al. |
| 6,775,007 B2 | 8/2004 | Izatt et al. |
| 6,863,667 B2 | 3/2005 | Webb et al. |
| 6,887,232 B2 | 5/2005 | Bille |
| 6,899,707 B2 | 5/2005 | Scholler et al. |
| 6,932,807 B1 | 8/2005 | Tomita et al. |
| 6,991,629 B1 | 1/2006 | Juhasz et al. |
| 6,996,905 B2 | 2/2006 | Meguro |
| 7,006,232 B2 | 2/2006 | Rollins et al. |
| 7,018,376 B2 | 3/2006 | Webb et al. |
| 7,027,233 B2 | 4/2006 | Goldstein et al. |
| 7,061,622 B2 | 6/2006 | Rollins et al. |
| 7,072,045 B2 | 7/2006 | Chen et al. |
| 7,072,047 B2 | 7/2006 | Westphal et al. |
| 7,079,254 B2 | 7/2006 | Kane et al. |
| 7,102,756 B2 | 9/2006 | Izatt et al. |
| 7,113,818 B2 | 9/2006 | Podoleanu et al. |
| 7,126,693 B2 | 10/2006 | Everett et al. |
| 7,130,054 B2 | 10/2006 | Ostrovsky et al. |
| 7,133,137 B2 | 11/2006 | Shimmick |
| 7,139,077 B2 | 11/2006 | Podoleanu et al. |
| 7,145,661 B2 | 12/2006 | Hitzenberger |
| 7,148,970 B2 | 12/2006 | de Boer |
| 7,184,148 B2 | 2/2007 | Alphonse |
| 7,207,983 B2 | 4/2007 | Hahn et al. |
| 7,248,371 B2 | 7/2007 | Chan et al. |
| 7,268,885 B2 | 9/2007 | Chan et al. |
| 7,280,221 B2 | 10/2007 | Wei |
| 7,307,733 B2 | 12/2007 | Chan et al. |
| 7,310,150 B2 | 12/2007 | Guillermo et al. |
| 7,312,876 B2 | 12/2007 | Chan et al. |
| 7,329,002 B2 | 2/2008 | Nakanishi |
| 7,330,270 B2 | 2/2008 | O'Hara et al. |
| 7,330,273 B2 | 2/2008 | Podoleanu et al. |
| 7,335,223 B2 | 2/2008 | Obrebski |
| 7,336,366 B2 | 2/2008 | Choma et al. |
| 7,342,659 B2 | 3/2008 | Horn et al. |
| 7,347,548 B2 | 3/2008 | Huang et al. |
| 7,352,444 B1 | 4/2008 | Seams et al. |
| 7,355,716 B2 | 4/2008 | de Boer et al. |
| 7,364,296 B2 | 4/2008 | Miller et al. |
| 7,365,856 B2 | 4/2008 | Everett et al. |
| 7,365,859 B2 | 4/2008 | Yun et al. |
| 7,370,966 B2 | 5/2008 | Fukuma et al. |
| 7,371,230 B2 | 5/2008 | Webb et al. |
| 7,372,578 B2 | 5/2008 | Akiba et al. |
| 7,388,672 B2 | 6/2008 | Zhou et al. |
| 7,390,089 B2 | 6/2008 | Loesel et al. |
| 7,400,410 B2 | 7/2008 | Baker et al. |
| 7,402,159 B2 | 7/2008 | Loesel et al. |
| 7,426,037 B2 | 9/2008 | Ostrovsky et al. |
| 7,433,046 B2 | 10/2008 | Everett et al. |
| 7,452,077 B2 | 11/2008 | Meyer et al. |
| 7,452,080 B2 | 11/2008 | Wiltberger et al. |
| 7,461,658 B2 | 12/2008 | Jones et al. |
| 7,466,423 B2 | 12/2008 | Podoleanu et al. |
| 7,470,025 B2 | 12/2008 | Iwanaga |
| 7,477,764 B2 | 1/2009 | Haisch |
| 7,480,058 B2 | 1/2009 | Zhao et al. |
| 7,480,059 B2 | 1/2009 | Zhou et al. |
| 7,488,070 B2 | 2/2009 | Hauger et al. |
| 7,488,930 B2 | 2/2009 | Ajgaonkar et al. |
| 7,492,466 B2 | 2/2009 | Chan et al. |
| 7,503,916 B2 | 3/2009 | Shimmick |
| 7,508,525 B2 | 3/2009 | Zhou et al. |
| 7,535,577 B2 | 5/2009 | Podoleanu et al. |
| 7,537,591 B2 | 5/2009 | Feige et al. |
| 7,557,928 B2 | 7/2009 | Ueno |
| 7,575,322 B2 | 8/2009 | Somani |
| 7,593,559 B2 | 9/2009 | Toth et al. |
| 7,602,500 B2 | 10/2009 | Izatt et al. |
| 7,604,351 B2 | 10/2009 | Fukuma et al. |
| 7,614,744 B2 | 11/2009 | Abe |
| 7,630,083 B2 | 12/2009 | de Boer et al. |
| 7,631,970 B2 | 12/2009 | Wei |
| 7,633,627 B2 | 12/2009 | Choma et al. |
| 7,643,152 B2 | 1/2010 | de Boer et al. |
| 2001/0022648 A1 | 9/2001 | Lai |
| 2002/0013574 A1 | 1/2002 | Elbrecht et al. |
| 2002/0082466 A1 | 6/2002 | Han |
| 2002/0097374 A1 | 7/2002 | Payne et al. |
| 2002/0133145 A1 | 9/2002 | Gerlach et al. |
| 2002/0198516 A1 | 12/2002 | Knopp |
| 2003/0206272 A1 | 11/2003 | Cornsweet et al. |
| 2004/0039378 A1 | 2/2004 | Lin |
| 2004/0059321 A1 | 3/2004 | Knopp et al. |
| 2004/0151466 A1 | 8/2004 | Crossman-Bosworth et al. |
| 2004/0243233 A1 | 12/2004 | Phillips |
| 2005/0010109 A1 | 1/2005 | Faul |
| 2005/0015120 A1 | 1/2005 | Seibel et al. |
| 2005/0021011 A1 | 1/2005 | LaHaye |
| 2005/0173817 A1 | 8/2005 | Fauver et al. |
| 2005/0192562 A1 | 9/2005 | Loesel et al. |
| 2005/0201633 A1 | 9/2005 | Moon et al. |
| 2005/0203492 A1 | 9/2005 | Nguyen et al. |
| 2005/0215986 A1 | 9/2005 | Chernyak et al. |
| 2005/0284774 A1 | 12/2005 | Mordaunt |
| 2005/0286019 A1 | 12/2005 | Wiltberger et al. |
| 2005/0288745 A1 | 12/2005 | Andersen et al. |
| 2006/0020172 A1 | 1/2006 | Luerssen et al. |
| 2006/0077346 A1 | 4/2006 | Matsumoto |
| 2006/0100613 A1 | 5/2006 | McArdle et al. |
| 2006/0179992 A1 | 8/2006 | Kermani |
| 2006/0187462 A1 | 8/2006 | Srinivasan et al. |
| 2006/0195076 A1* | 8/2006 | Blumenkranz et al. ........... 606/4 |
| 2006/0206102 A1 | 9/2006 | Shimmick |
| 2007/0013867 A1 | 1/2007 | Ichikawa |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0147730 A1 | 6/2007 | Wiltberger et al. |
| 2007/0173791 A1 | 7/2007 | Raksi |
| 2007/0173794 A1 | 7/2007 | Frey et al. |
| 2007/0173795 A1 | 7/2007 | Frey et al. |
| 2007/0185475 A1 | 8/2007 | Frey et al. |
| 2007/0189664 A1 | 8/2007 | Andersen et al. |
| 2007/0216909 A1 | 9/2007 | Everett et al. |
| 2007/0219541 A1 | 9/2007 | Kurtz |
| 2007/0230520 A1 | 10/2007 | Mordaunt et al. |
| 2007/0291277 A1 | 12/2007 | Everett et al. |
| 2007/0299429 A1 | 12/2007 | Amano |

| | | | |
|---|---|---|---|
| 2008/0033406 | A1 | 2/2008 | Andersen et al. |
| 2008/0049188 | A1 | 2/2008 | Wiltberger et al. |
| 2008/0055543 | A1 | 3/2008 | Meyer et al. |
| 2008/0056610 | A1 | 3/2008 | Kanda |
| 2008/0071254 | A1 | 3/2008 | Lummis et al. |
| 2008/0088795 | A1 | 4/2008 | Goldstein et al. |
| 2008/0100612 | A1 | 5/2008 | Dastmalchi et al. |
| 2008/0281303 | A1 | 11/2008 | Culbertson et al. |
| 2008/0281413 | A1 | 11/2008 | Culbertson et al. |
| 2008/0319427 | A1 | 12/2008 | Palanker |
| 2009/0012507 | A1 | 1/2009 | Culbertson et al. |
| 2009/0088734 | A1 | 4/2009 | Mordaunt |
| 2009/0131921 | A1 | 5/2009 | Kurtz et al. |
| 2009/0149742 | A1 | 6/2009 | Kato et al. |
| 2009/0157062 | A1 | 6/2009 | Hauger et al. |
| 2009/0161827 | A1* | 6/2009 | Gertner et al. ............ 378/65 |
| 2009/0168017 | A1 | 7/2009 | O'Hara et al. |
| 2009/0268161 | A1 | 10/2009 | Hart et al. |
| 2010/0004641 | A1 | 1/2010 | Frey et al. |
| 2010/0004643 | A1 | 1/2010 | Frey et al. |
| 2010/0007848 | A1 | 1/2010 | Murata |
| 2010/0022994 | A1 | 1/2010 | Frey et al. |
| 2010/0022995 | A1 | 1/2010 | Frey et al. |
| 2010/0022996 | A1 | 1/2010 | Frey et al. |
| 2010/0042079 | A1 | 2/2010 | Frey et al. |
| 2010/0110377 | A1 | 5/2010 | Maloca et al. |
| 2010/0324543 | A1 | 12/2010 | Kurtz et al. |
| 2011/0022036 | A1 | 1/2011 | Frey et al. |
| 2011/0118609 | A1 | 5/2011 | Goldshleger et al. |
| 2011/0319873 | A1 | 12/2011 | Raksi et al. |
| 2012/0274903 | A1* | 11/2012 | Sayeram et al. ............ 351/208 |

FOREIGN PATENT DOCUMENTS

| | | |
|---|---|---|
| WO | 98/08048 | 2/1998 |
| WO | 2006074469 | 7/2006 |
| WO | WO2007106326 | 9/2007 |
| WO | 2007/130411 | 11/2007 |

OTHER PUBLICATIONS

Arimoto et al., "Imaging Properties of Axicon in a Scanning Optical System," Nov. 1, 1992, Applied Optics, 31(31): 6652-6657, 5 pages.

Birngruber et al., "In-Vivo Imaging of the Development of Linear and Non-Linear Retinal Laser Effects Using Optical Coherence Tomography in Correlation with Histopathological Findings," 1995, Proc. SPIE 2391:21-27, 7 pages.

Chinn, S.R., et al., "Optical coherence tomography using a frequency-tunable optical source," *Optics Letters*, 22(5):340-342, Mar. 1997.

Fercher et al., "Eye-Length Measurement by Interferometry With Partially Coherent Light," Mar. 1988, Optics Letters, 13(3):186-188, 3 pages.

Fercher et al., "Measurement of Intraocular Distances by Backscattering Spectral Interferometry," May 15, 1995, Optics Comm. 117:43-48, 6 pages.

Huber, R., et al., "Three-dimensional and C-mode OCT imaging with a compact, frequency swept laser source at 1300 nm," *Optics Express*, 13(26):10523-10538, Dec. 2005.

International Search Report and Written Opinion dated Mar. 12, 2009 for International Application No. PCT/US2008/075511, filed Sep. 5, 2008 (9 pages).

Izatt et al., Micron-Resolution Biomedical Imaging With Optical Coherence Tomography, Oct. 1993, Optics & Photonics News, pp. 14-19, 6 pages.

Massow, O., et al., "Femtosecond laser microsurgery system controlled by optical coherence tomography," *Proceedings of the SPIE—Commercial and Biomedical Applications of Ultrafast Lasers VIII*, vol. 6881, pp. 688106(1)-688106(6), Mar. 2008, 6 pages.

Massow, O., et al., "Optical coherence tomography controlled femtosecond laser microsurgery system," *Proceedings of the SPIE—Optical Coherence Tomography and Coherence Techniques III*, vol. 6627, pp. 662717(1)-662717(6), Aug. 2007.

Ohmi, M., et al., "In-situ Observation of Tissue Laser Ablation Using Optical Coherence Tomography," *Optical and Quantum Electronics*, 37(13-15):1175-1183, Dec. 2005, 9 pages.

Sarunic, M., et al., "Imaging the Ocular Anterior Segment With Real-Time, Full-Range Fourier-Domain Optical Coherence Tomography," *Archives of Ophthalmology*, 126(4):537-542, Apr. 2008, 6 pages.

Sarunic, M., et al., "Instantaneous complex conjugate resolved spectral domain and swept-source OCT using 3×3 fiber couplers," *Optics Express*, 13(3):957-967, Feb. 2005 11 pages.

Sarunic, M., et al., "Real-time quadrature projection complex conjugate resolved Fourier domain optical coherence tomography," *Optics Letters*, 31(16):2426-2428, Aug. 2006.

Stern et al., "Femtosecond Optical Ranging of Corneal Incision Depth," Jan. 1989, Investigative Ophthalmology & Visual Science, 30(1):99-104, 6 pages.

Swanson, et al., "Method and Apparatus for Optical Imaging with Means for Controlling the Longitudinal Range of the Sample," U.S. Appl. No. 90/006,816, filed Oct. 20, 2003.

Tao, Y., et al., "High-speed complex conjugate resolved retinal spectral domain optical coherence tomography using sinusoidal phase modulation," *Optics Letters*, 32(20):2918-2920, Oct. 2007, 3 pages.

Tommaseo, Giovanni, Examiner, Eurepean Patent Office, European Patent Application No. 10191057.8, in European Search Report, mailed Mar. 16, 2011, 3 pages.

Wojtkowski et al., "In Vivo Human Retinal Imaging by Fourier Domain Optical Coherence Tomography," Jul. 2002, Journal of Biomedical Optics 7(3):457-463, 7 pages.

Yun, S.H., et al., "Wavelength-swept fiber laser with frequency shifted feedback and resonantly swept intra-cavity acoustooptic tunable filter," *IEEE Journal of Selected Topics in Quantum Electronics*, 3(4):1087-1096, Aug. 1997.

PCT International Search Report and Written Opinion dated Feb. 9, 2012 for International Application Serial No. PCT/US2011/040223.

Kim, Tae Hoon, Authorized Officer, Korean Intellectual Property Office, PCT International Application No. PCT/US2011/025332, in International Search Report, mailed Sep. 16, 2011, 8 pages.

Kim, Tae Hoon, Authorized Officer, Korean Intellectual Property Office, PCT International Application No. PCT/US2011/023710, in International Search Report, mailed Aug. 24, 2011, 8 pages.

Partial International Search Report corresponding to PCT Application Serial No. PCT/US2012/035927 dated Aug. 3, 2012.

Hee, M., et al., "Fenntosecond Transillumination Optical Coherence Tomography," Optics Letters, Jun. 1993, pp. 950-952, 18(12).

PCT International Search Report and Written Opinion dated Apr. 10, 2012 for International Application No. PCT/US2011/051466, filed Sep. 13, 2011.

* cited by examiner

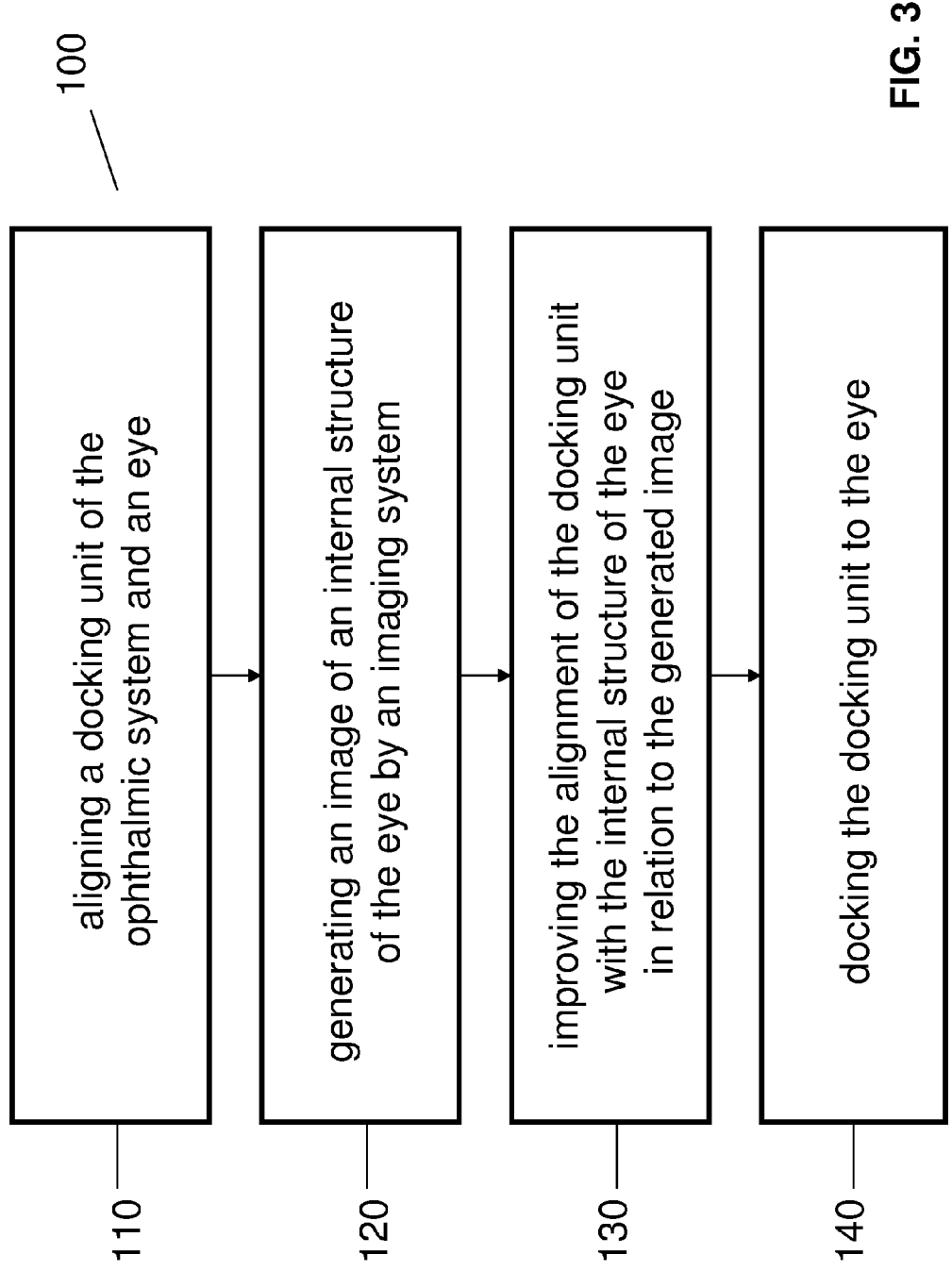

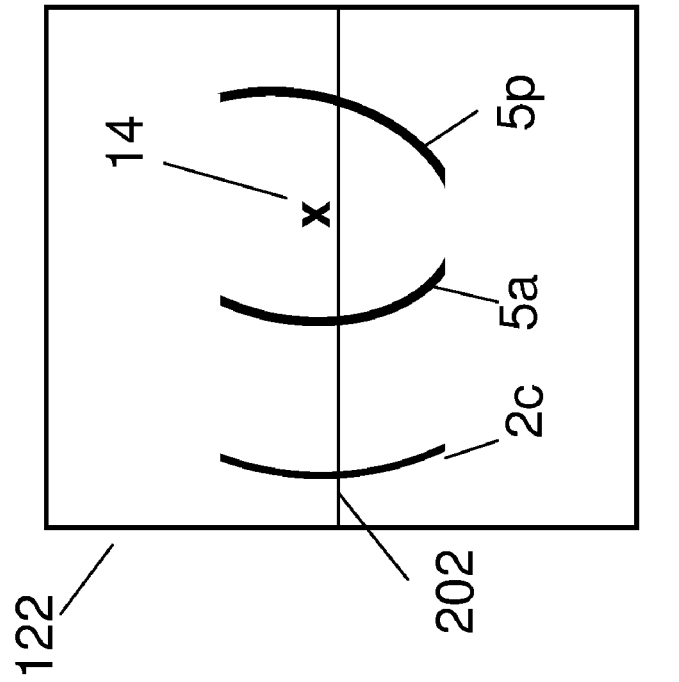
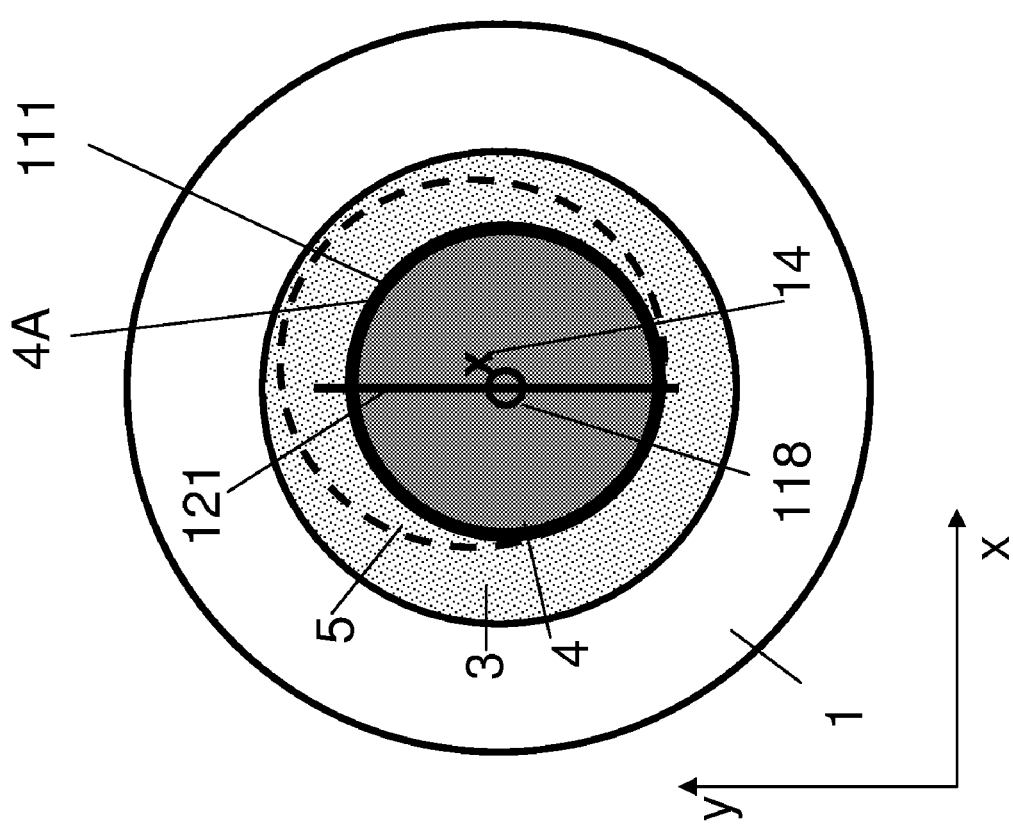
FIG. 6B
FIG. 6A

IMAGE-GUIDED DOCKING FOR OPHTHALMIC SURGICAL SYSTEMS

TECHNICAL FIELD

This patent document relates to systems and techniques for surgical applications, including ophthalmic surgery. In more detail, the patent document relates to systems and methods for docking ophthalmic surgical systems to a surgical eye with high precision.

BACKGROUND

A variety of advanced surgical laser systems have been developed over the years for ophthalmic surgery, targeting portions of the cornea, the lens, the retina and other structures of the eye. Some of these surgical systems increase the precision of the surgical procedure by creating a well-controlled connection between the ophthalmic surgical apparatus and the ophthalmic target, typically a region or a structure of the eye. In some cases this connection is established by lowering a docking module or unit onto the eye. Certain systems also employ an additional fixation step, such as the application of suction to strengthen the connection. In typical surgical laser systems the precision and control of the ophthalmic surgery is substantially impacted by the precision of these docking and fixation steps and hence improving the precision of the docking procedure can improve the precision of the entire ophthalmic surgical procedure.

SUMMARY

This patent document discloses examples and implementations of systems and techniques for guiding an ophthalmic surgical system to create a well-controlled connection with an ophthalmic target, such as a human eye.

For example, a docking method for an ophthalmic system may include the steps of aligning a docking unit of the ophthalmic system and an eye; generating an image of an internal structure of the eye by an imaging system; improving an alignment of the docking unit with the internal structure of the eye in relation to the generated image; and docking the docking unit to the eye.

The aligning the docking unit step may include using a first imaging system to align a target pattern of the ophthalmic system in relation to a feature of the eye.

The first imaging system can be one of a microscope or a video microscope; the target pattern of the ophthalmic system can include at least one of a center of a contact lens, a center of the docking unit, a docking circle, or a docking cross-hair; and the feature of the eye may be a center of a region of an iris, a pupil, a cornea, a limbus, or a lens; or a circular formation related to a region of the iris, the pupil, the cornea, the limbus or the lens.

The generating an image step may include generating an image with a second imaging system, wherein the second imaging system is one of an optical coherence tomographic imaging system and an imaging system configured to image the internal structure of the eye.

The improving an alignment step may include extracting position information regarding the internal structure of the eye from the generated image; and adjusting a position of at least one of the eye or the docking unit in relation to the extracted position information.

The improving an alignment step may include extracting orientation information regarding the internal structure of the eye from the generated image; and adjusting an orientation of at least one of the eye or the docking unit in relation to the extracted orientation information.

The generating the image step may include computing scanning data by a processor corresponding to a scanning pattern; storing the scanning data in a data buffer; transferring the scanning data by the data buffer to an output module; outputting scanning signals by the output module to one or more scanners based on the scanning data; and scanning an imaging beam with the one or more scanners according to the scanning signals.

The computing the scanning data step may include implementing a scanning pattern that includes at least one of a linear pattern, a circular pattern, an oval pattern, a loop pattern, an arc pattern, a raster pattern, an x-y pattern, a crosshair pattern, a star pattern, a spiral pattern, and a pattern with outlying points.

The computing the scanning data step may include inserting synchronizing signals into the scanning data by the processor.

The computing the scanning data step may include computing homing data corresponding to a homing pattern connecting a starting point of the scanning pattern to a previously set point.

The storing the scanning data step may include storing the scanning data in a processor memory; and transferring the stored scanning data from the processor memory to the data buffer partially under the control of a dedicated memory controller.

The dedicated memory controller may include a direct memory access engine; and the data buffer may include a first-in-first-out memory.

The transferring the scanning data step may include outputting the scanning data by the data buffer to the output module in a fast data transfer mode.

The transferring the scanning data step may include outputting the scanning data from the data buffer without sending the scanning data through at least one of a bus connecting the dedicated memory controller and the processor, the processor memory, or the processor.

The transferring the scanning data step may include outputting the scanning data in parallel with the processor performing at least one of processing an image, computing scanning data corresponding to a scanning pattern, or performing a control function.

The transferring the scanning data step may include receiving the scanning data by the output module without an interrupt by another system agent, thereby keeping a jitter of the scanning data below 40 microseconds.

The outputting the scanning signals step may include converting the scanning data into analog scanning signals by the output module, wherein the output module includes a digital-analog converter.

The scanning an imaging beam step may include receiving the outputted scanning signals by a scanning controller and an imaging synchronizer, wherein the scanning signals comprise synchronizing signals; repeatedly adjusting the one or more scanners by the scanning controller according to the scanning signals to scan the imaging beam; and repeatedly synchronizing an imaging camera by the imaging synchronizer according to the synchronizing signals.

The scanning controller may include at least one galvo-controller; and the imaging synchronizer may include at least one ophthalmic coherence imaging camera controller.

In some implementations an integration time of an image recording device can be a limiting factor of an operating speed of an imaging system.

The outputting the scanning signals step may include outputting the scanning signals at a rate within one of the following ranges: 1 Hz-1 MHz, 100 Hz-1 MHz, or 1 kHz-100 kHz.

The outputting the scanning signals step may include adjusting an output rate of the output of the scanning signals.

The improving the alignment step may include providing a verbal command to a patient to move his eye, moving the patient's head, moving a surgical bed the patient is resting on, moving the patient's eye, moving the docking unit via moving a gantry or an articulated arm, and using a gripper to move the eye, based on the image of the internal structure of the eye.

The improving the alignment step may include adjusting at least one of a fixation beam or a directing light to improve the alignment of the eye and the docking unit; and directing the patient to follow the fixation beam or the directing light with his eye.

The improving the alignment step may include starting the improving the alignment step before the docking unit makes contact with the eye, after the docking unit makes contact with the eye but before an application of a partial vacuum to the docking unit, or after an application of a partial vacuum.

The docking step may include sensing a distance between a reference point of the docking unit and an outer layer of the eye; and lowering the docking unit according to the sensed distance.

In some implementations the reference point can be adjustable.

The docking step may include bringing the docking unit into physical contact with the eye; and applying suction through a portion of the docking unit after the docking unit makes physical contact with the eye.

In some implementations an imaging controller for an ophthalmic system may include a processor that computes scanning data for a scanning pattern; a local memory controller that partially manages a transfer of the computed scanning data from the processor to a data buffer, wherein the data buffer is configured to store the scanning data and to output the scanning data; and an output digital-analog converter, coupled to the data buffer that converts selected scanning data to analog scanning signals and outputs the scanning signals.

The local memory controller may include a direct memory access engine.

The data buffer may include a first-in-first-out memory that outputs the stored scanning data in a fast data transfer mode.

The imaging controller may further include a processor memory; and a bus, coupled to the processor, the local memory controller and the processor memory, wherein the processor is configured to output the computed scanning data to the processor memory through the bus; and the local memory controller is configured to transfer the scanning data from the processor memory to the data buffer through the bus.

In some implementations the data buffer is configured to output the scanning data without sending the scanning data through at least one of the bus, the processor memory, or the processor.

In some implementations the processor is configured to perform at least one of processing an image and computing scanning data, while the data buffer outputs the scanning data.

In some implementations the output digital-analog converter is coupled to the data buffer so that the scanning data, outputted by the data buffer is received without an interrupt by another system agent, thereby keeping a jitter of the scanning data below 40 microseconds.

In some implementations the output digital-analog converter is configured to output the scanning signals to x and y scanning controllers to scan an imaging beam; and synchronizing signals to an imaging camera to record a returned imaging beam synchronously with the scanning.

In some implementations a method of controlling an ophthalmic imaging may include computing scanning control data by a processor; storing the scanning control data into a data buffer partially under the control of a memory controller; transferring the scanning control data from the data buffer to a signal converter through a dedicated channel; and sending scanning signals to a scanning controller by an output module, wherein the scanning signals are converted from the scanning control data by the signal converter.

The storing the scanning control data step may include storing the computed scanning control data in a processor memory; and moving the scanning control data from the processor memory to the data buffer.

The transferring the scanning control data step may include transferring the scanning data from the data buffer without sending the scanning data through at least one of a bus connecting the local memory controller and the processor, the processor memory, or the processor.

The transferring the scanning control data step may include transferring the scanning data in parallel with the processor performing at least one of processing an image; and computing scanning data corresponding to a scanning pattern.

The transferring the scanning control data step may include transferring the scanning data without an interrupt by another system agent, thereby keeping a jitter of the scanning data below 40 microseconds.

The local memory controller may include a direct memory access engine; and the data buffer may be a first-in-first-out memory.

BRIEF DESCRIPTION OF THE DRAWINGS

FIG. 3 illustrates a docking method.
FIGS. 6A-B illustrate a tilted and displaced lens and its image.

DETAILED DESCRIPTION

Many ophthalmic surgical systems include a docking unit, or patient interface, that makes contact with a surgical eye and keeps it effectively immobile relative to an objective of the surgical system during an ophthalmic procedure. The precision of the ophthalmic procedure can be increased by increasing the precision of the alignment of the docking unit with the target of the surgery.

In corneal procedures, where the surgical target—the cornea—is unobstructed and visible, aligning the patient interface with the target can be performed by the surgeon in a relatively straightforward manner.

However, cataract surgeries pose harder challenges for the alignment and docking of the patient interface for several reasons. These challenges include that the targeted lens is located inside the eye and thus it is less visible for, or partially obstructed from the surgeon.

Also, patients often have difficulties aligning their surgical eye with the optical axis of the ophthalmic surgical system even if given guidance and verbal instructions by the surgeon, as e.g. often the patients are given muscle relaxants or are under heavy sedation.

Further, internal eye structures, such as the lens, are often held by their soft support muscles off-center and tilted relative to the visible structures of the eye, such as the pupil. Therefore, even if a surgeon manages to align the pupil with the optical axis of the surgical system, the lens inside the eye may be still displaced and tilted.

Moreover, as the docking unit is lowered to the eye, it exerts pressure on the eye, possibly resulting in additional displacement and tilting of the lens. This problem can be exacerbated even further by applying suction to dock the patient interface.

Implementations and embodiments in this patent document provide docking procedures and systems for increasing the precision of the docking procedure of ophthalmic surgeries by imaging techniques.

Figure 1:
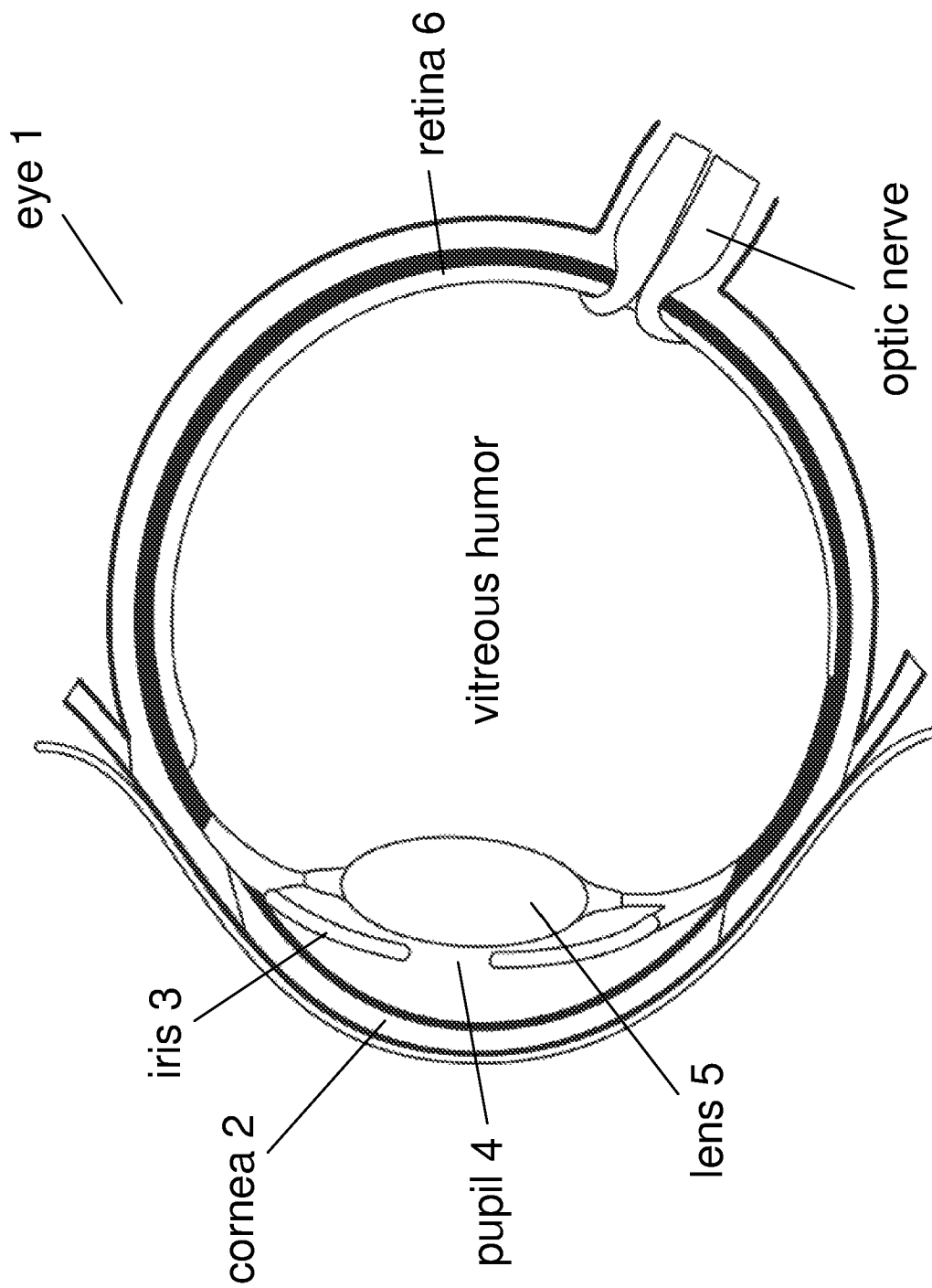
FIG. 1 illustrates the human eye.

FIG. 1 illustrates a human eye 1 in some detail. The eye 1 includes a cornea 2 that receives and refracts the incoming light, an iris 3, a pupil 4 that provides an opening for the light to enter the inner eye and a lens 5 that focuses the light on the retina 6. As stated above, the lens 5 is often not aligned with the pupil 2, and its soft supporting ciliary muscle-system can allow additional displacement and tilt when the eye 1 is pressured by the docking unit, exacerbating the problem of misalignment with the docking unit.

Implementations and embodiments in this patent document provide docking procedures and systems for increasing the precision of the docking procedure of ophthalmic surgeries by imaging techniques.

Figure 2:
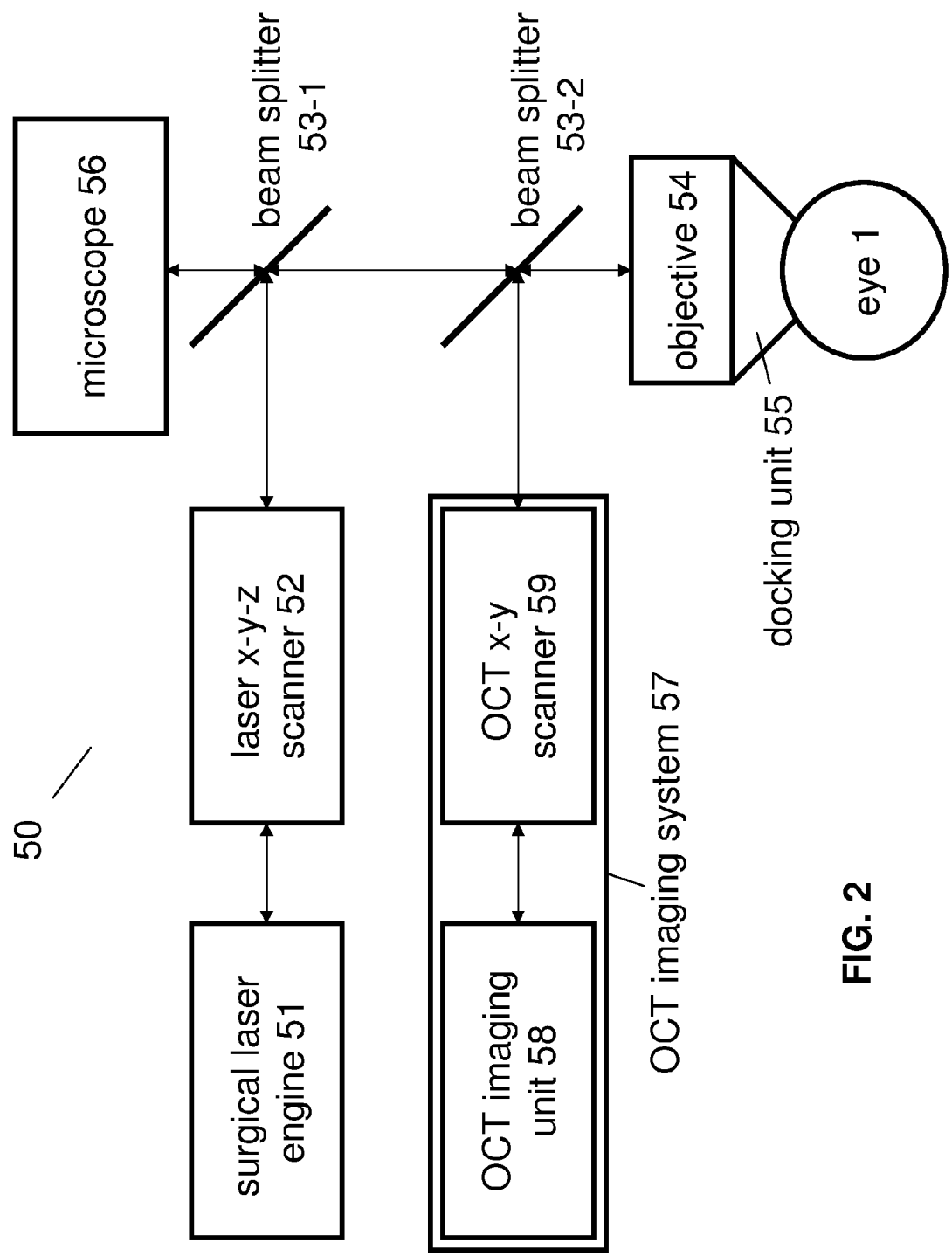
FIG. 2 illustrates an ophthalmic surgical system.

FIG. 2 illustrates an ophthalmic laser surgical system 50. The surgical system 50 can include a surgical laser engine 51 that generates the surgical laser beam. The surgical laser beam can be scanned across the surgical target region by a laser x-y-z scanner 52. The surgical laser beam can be coupled into the main system optical path by a beam splitter 53-1, redirecting it to an objective 54. The objective 54 can be part of or may contain a delivery tip, distal end, or lens cone.

In some implementations, parts of the laser x-y-z scanner 52, such as a z scanner block, can be located after the beam splitter 53-1 in the optical path. The z scanner block can be a separate unit, or may include more than one block, or can be part of the objective 54. Each of the x, y, and z scanners may contain more than one functional unit. For example, multiple minors can be used to perform the scanning in the x direction or the y direction, or multiple and separate lens groups can be used for an optimized z scanning.

A docking unit 55 can be removably appended to the objective 54 to make contact with the eye 1 to increase the precision of the targeting of the surgical laser beam into the surgical target region in the eye. The docking unit may be integrated into one piece or may contain more than one piece. A first part of a multi-piece docking unit can be first attached to the surgical eye, whereas a second part of the docking unit can be first attached to the objective 54, or a delivery tip. Subsequently, the first and second parts of the docking unit can be locked together. The docking unit 55 may be referred to as a patient interface, application tip, docking tip, lens cone, or applanation device, and may contain a contact lens or applanation lens which may make a contact with the eye or can be disposed close to the eye.

The surgical and docking procedures can be assisted by various imaging systems. In some surgical systems 50, a first imaging system, such as an ophthalmic surgical stereo microscope or video microscope 56, can be provided to image the surgical target region for the surgeon. The (ophthalmic or video) microscope 56 may make use of an observational or imaging light.

The imaging light may share part of the main optical path of the surgical system 50, or can be projected directly to the target region. In a shared-path implementation, the observational light can be generated close to the microscope 56, subsequently guided to the eye and returned from the eye, entering the main optical path or optical train of the surgical system 50 through the beam splitter 53-1. In a non-shared-path implementation, the imaging light can be generated close to and outside the objective 54 and directly projected onto portions of the eye. In this embodiment only the returned portion of the imaging light may be guided through the main optical pathway of the system to the microscope 56.

Some implementations may include a second imaging system in the surgical system 50 to provide imaging data about the inner structures of the eye and the target region. Using the images from the first and second imaging systems in synergy can provide enhanced guidance for the ophthalmic procedure in general and improve the accuracy of the docking of the patient interface in particular.

In some surgical systems 50 the second imaging system can be an optical coherence tomography (OCT) imaging system 57. The OCT imaging system 57 can be a time-domain, a swept-source or a spectrometer based OCT imaging system, among others. The OCT imaging system 57 can include an OCT imaging unit 58 that creates an OCT imaging beam, guides the OCT imaging beam toward the eye and processes the OCT imaging beam returned from the eye. The OCT imaging system 57 can also include an OCT x-y scanner 59 that scans the OCT imaging beam across the target region in the x-y plane which can be e.g. perpendicular to the optical axis.

In general, the notation "x-y-z" is used in a broad sense throughout this document: it can refer to scanning in three directions which make substantial angles with each other. These angles, however, may not be necessarily right angles. Also, the scanning may be performed along either straight or curved lines, on flat or curved surfaces in a grid, raster, concentric, spiral, or any other pattern. In some implementations the OCT imaging beam may be scanned by the surgical laser x-y-z scanner 52. In others, only some of the scanning functionalities of the surgical laser beam and the OCT imaging beam are performed by a shared scanner block, such as the x-y scanning functionality. Some OCT systems, such as time domain OCT systems require a z scanning of the beam, whereas others, such as spectrometer based OCT systems, do not require z scanning as they capture image data from all depth at essentially the same time.

The OCT imaging beam can be coupled into the main optical path of the surgical system 50 through a beam splitter 53-2, and directed into the target region by the objective 54 and docking unit 55. In some implementations, part or all of the z scanning functionality can be performed by a z scanner disposed in the shared optical path, after the beam splitter 53-2. The z scanner can be even part of the objective 54.

FIG. 3 illustrates a docking method 100 for the ophthalmic laser surgical system 50, where the docking method 100 may include:

An aligning step 110 for aligning the docking unit 55 of the ophthalmic system 50 and the eye;

An imaging step 120 for generating an image of an internal structure of the eye by an imaging system;

An alignment-improving step 130 for improving the alignment of the docking unit 55 with the internal structure of the eye in relation to the generated image; and A docking step 140 for docking the docking unit 55 to the eye.

These steps are described in detail below.

The aligning step 110 may include using the first imaging system to align a target pattern of the ophthalmic laser surgical system 50 with a feature of the eye. This aligning step 110 can be performed e.g. in relation to lowering the docking unit 55 towards the eye. The first imaging system may be the ophthalmic surgical microscope or video microscope 56.

The target pattern of the ophthalmic laser surgical system 50 can include at least one of a mark of a center of a contact lens, of a center of the docking unit 55, or of an optical axis of the objective 54, the docking unit 55 or the contact lens. In other implementations, it can include a docking circle, a docking cross-hair, or any other docking target pattern, as well as a combination of the above patterns. This target pattern can be formed in the optics of an ophthalmic surgical microscope 56, or can be electronically generated and displayed on a display or screen of a video microscope 56.

The feature of the eye can be a center of a region of the cornea 2, the iris 3, the pupil 4, a limbus, a sclera, or the lens 5; or a circular formation related to a region of the cornea 2, the iris 3, the pupil 4, the limbus, the sclera, or the lens 5.

Figures 4A, 4B:
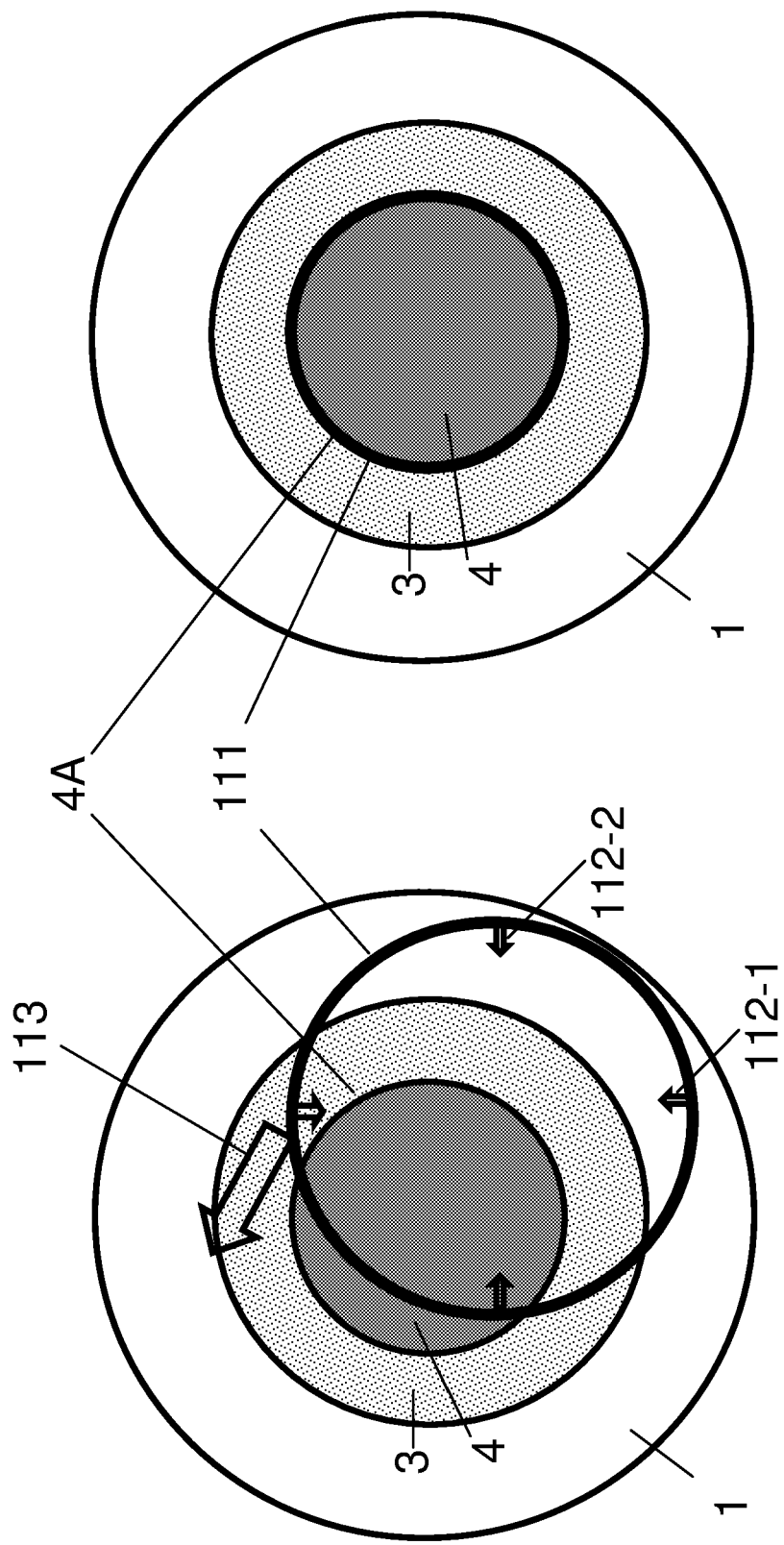
FIGS. 4A-B illustrate an aligning step.

FIGS. 4A-B show an illustrative example of the aligning step 110. In FIG. 4A, the video microscope 56 displays the eye 1 as seen through the objective 54 of the laser surgical system 50, and a variable radius target pattern circle 111, centered at the shared optical axis of the objective 54 and docking unit 55. As the surgeon lowers the docking unit 55 towards the eye, in a pattern adjusting step 112 he may adjust the variable radius of the target pattern circle 111 to be essentially equal to the radius of the inner circular edge 4A of the patient's pupil 4, as indicated by the arrows 112-1 and 112-2. In addition, in a pattern moving step 113, the surgeon may also adjust or move the docking unit 55 in the x-y plane, as shown by the arrow 113, to align the target pattern circle 111 with the inner circular edge 4A of the pupil 4 before, during or after the radius adjustment.

The radius of the target pattern circle 111 can be chosen to be somewhat different from the radius of the inner circular edge 4A of the pupil 4 as long as the radius enables the surgeon to align the target pattern circle 111 with the pupil 4 with a desired precision. In other embodiments, any other target pattern can be used, including arcs, cross-hairs, and raster patterns, as listed above.

FIG. 4B illustrates that the adjusting of the variable radius of the target pattern circle 111 in step 112 and the moving of the docking unit 55 in the x-y plane in step 113 may be repeatedly and iteratively performed until the target pattern circle 111 essentially coincides with the inner circular edge 4A of the pupil 4. Doing so aligns the shared optical axis of the objective 54 and the docking unit 55 with the axis or center of the pupil 4.

During this aligning step 110 the docking unit 55 may get lowered toward the eye, possibly even getting into physical contact with the eye during an adjustment of the z directional position of the docking unit 55. However, in either case the docking unit 55 still can remain movable relative to the eye, allowing the surgeon to carry out the aligning step 110, possibly iteratively. Even at the end of aligning step 110 the docking unit may remain movably connected to the eye to allow for a possible subsequent aligning step.

In some implementations, the aligning step 110 may not involve a target pattern. In these cases the alignment of the docking unit 55 may be guided primarily by the visual assessment of the surgeon.

Embodiments of this aligning step 110 align the docking unit 55 and the eye to a certain precision. If the docking unit is docked to the eye after aligning step 110, an ophthalmic procedure can be performed with a certain precision. For some procedures this precision may be sufficient, but others may benefit from a higher precision.

Figure 5:
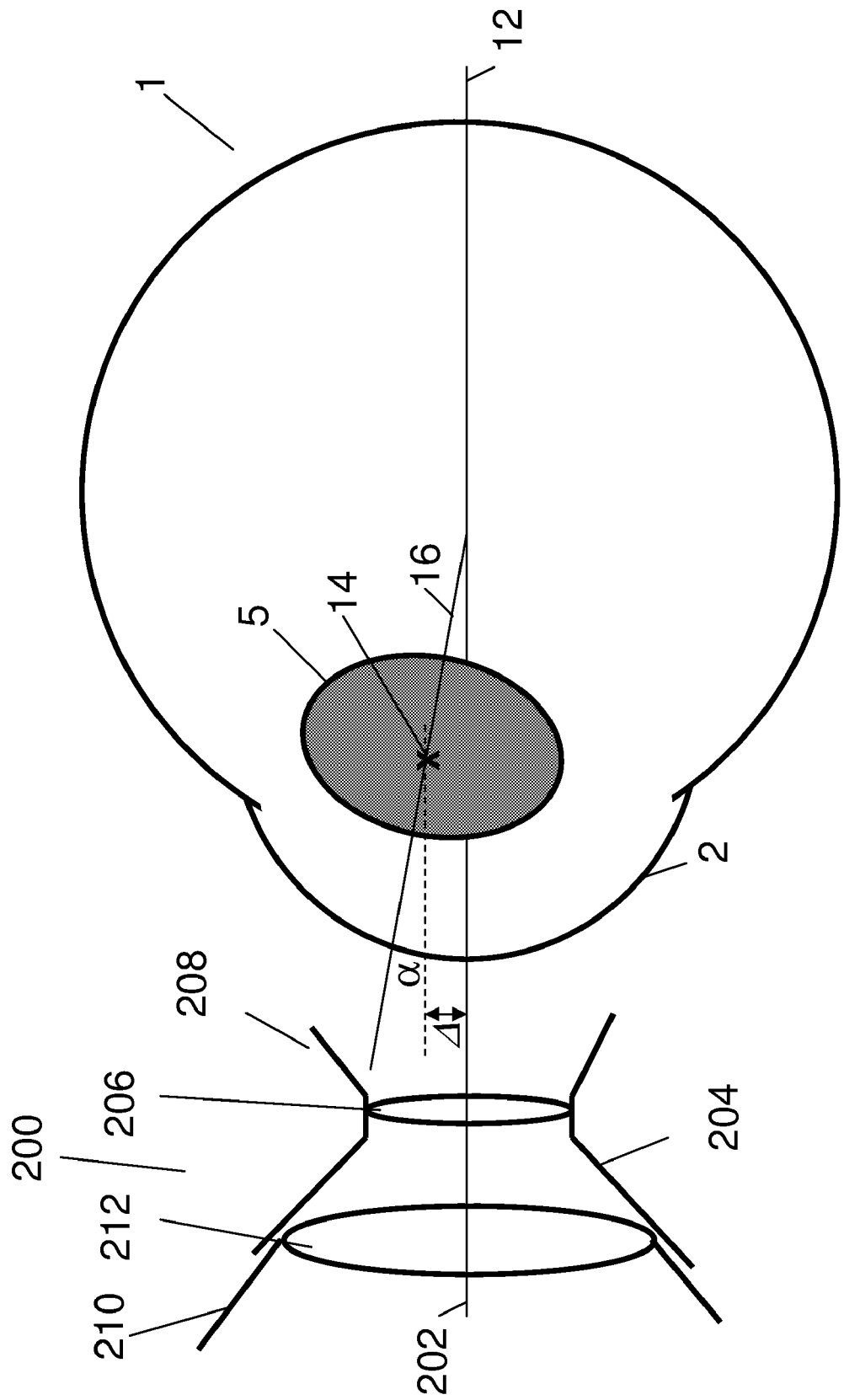
FIG. 5 illustrates the tilt and displacement of a lens relative to the docking unit.

FIG. 5 illustrates such a situation. Even after an optical axis 202 of a docking unit 200 is aligned with the pupil 4 of the eye in the aligning step 110, the lens 5 of the eye may remain displaced and tilted relative to the optical axis 202, as the lens 5 may not be aligned with the pupil 4 for one of the reasons outlined above. Here, the docking unit 200 can be an embodiment of the docking unit 55.

In FIG. 5, even after an optical axis 12 of the pupil 4 and the eye has been aligned with the optical axis 202 of the docking unit 200 in the aligning step 110, a center 14 of the lens 5 is still offset by $\Delta$ from the shared optical axis 12/202 of the pupil 4 and the docking unit 200, and a symmetry axis 16 of the lens 5 still makes an angle $\alpha$ with the shared optical axis 12/202.

Here, the body or housing 204 of the docking unit 200, sometimes called patient interface, lens cone, or application tip, may contain a contact lens, applanation lens or applanation plate 206 and a skirt or flexible seal 208, which makes contact with the outer eye-surface, typically with the cornea, limbus, or sclera. The docking unit 200 can be affixed to an embodiment of the objective, delivery tip, or distal end 210 or 54, which may include several lenses, the ultimate lens being distal lens 212.

FIGS. 6A-B illustrate the imaging step 120 in some detail.

FIG. 6A illustrates that in the aligning step 110 the docking unit 55 or 200 can be properly aligned and centered with the pupil 4 using the video microscope 56, as evidenced by the target pattern circle 111 overlapping with the inner circular edge 4A of the pupil 4, and its center 118 (denoted by a circle) being at the center of the pupil 4. However, the lens 5, shown with a dotted line as its outer perimeter is hidden from the view of the video microscope 56, can be off-center with respect to the pupil 4. This is indicated also by the center 14 of the lens, denoted by an x, being off the center 118 of the target pattern 111, denoted by the circle. Furthermore, the axis 16 of the lens 5 can be tilted relative to the shared axis 202/12 of the docking unit 200 and pupil 4.

Therefore, even after the aligning step 110, the target pattern circle 111 may not be well-aligned with the lens 5, and thus the precision of cataract procedures centered with the target pattern circle 111 may not be optimal. This non-optimal precision can be improved by performing the imaging step 120.

FIGS. 6A and B illustrate that in a typical case, the imaging step 120 can include a linear scan 121 across the center 118 of the target pattern circle 111 which coincides with the center of the pupil 4. This linear scan 121 generates a y-z image 122 that includes an image 2c of a corneal segment and images 5a and 5p of segments of the anterior and posterior lens capsule, respectively. The images of the lens segments 5a and 5p appear tilted and off center relative to the optical axis 202 in the y-z image 122, even if the corneal segment image 2c appears centered, since the lens 5 can be tilted and off-center relative to the cornea and pupil. Therefore, providing the images of the lens segments 5a and 5p may help the surgeon to improve the alignment of the docking unit 200 with the tilted and off-center lens 5.

In other implementations, the imaging step 120 can involve generating an image with a line scan along a linear pattern, an arc, a crosshair pattern, a star pattern, a circular pattern, an oval pattern, a loop pattern, a spiral pattern, a concentric multi-circle pattern, a shifted multi-circle pattern, a line pattern, and with a two dimensional scan along an x-y, raster or grid scanning pattern and a pattern with outlying points.

The imaging step 120 can involve generating an image with an embodiment of the optical coherence tomographic (OCT) imaging system 57, as described in detail above and below. The imaging step 120 can be also performed with another imaging system, capable of imaging an internal structure of the eye.

Figure 7:
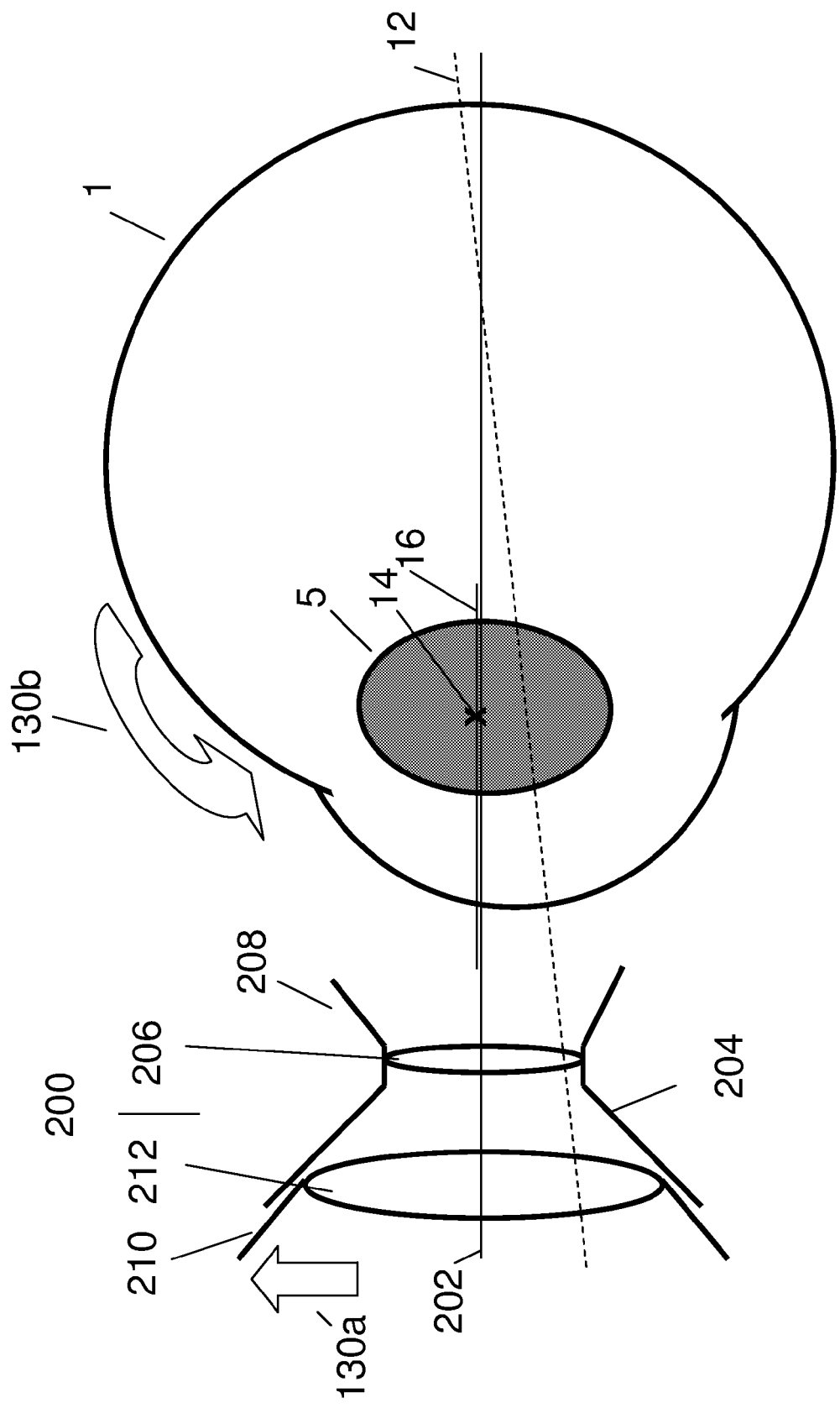
FIG. 7 illustrates an improvement of the alignment between the lens and the docking unit.

FIG. 7 illustrates that the alignment of the docking unit 200 with the lens 5 can be improved by the alignment-improving step 130, based on the imaging step 120.

In one aspect, the alignment-improving step 130 can include extracting position information regarding the lens 5 from the generated image 122, and adjusting a position of at least one of the eye 1 or the docking unit 200 in relation to the extracted position information. In some implementations, other internal eye-structures can be targeted, such as the nucleus of the lens, or a retinal structure.

In an implementation, the surgeon can analyze the y-z image 122, generated by the imaging step 120, and determine the offset $\Delta$ of the lens center 14 from the optical axis 202 of the docking unit 200. Based on this determination, the surgeon can shift either the eye, or the docking unit, or both, to overcome this $\Delta$ offset, as indicated by arrow 130a. This adjustment-improving step 130 can reduce or even eliminate the offset $\Delta$ between the lens center 14 and the optical axis 202. Typically, this shift 130a can offset the optical axis 202 of the docking unit 200 from the optical axis 12 of the lens 5.

The shift 130a may be performed iteratively because in the first try the surgeon may not have determined the offset $\Delta$ precisely. To remedy this, in some implementations the alignment-improving step 130 may be followed by a repeated imaging step 120' to determine how the offset $\Delta'$ was changed by the shift 130a. This repeated imaging step 120' can be followed by a repeated alignment-improving step 130' based on the updated image 122' generated by the repeated imaging step 120', and so on. In efficient implementations, the offset $\Delta$ is reduced step-by-step. In other implementations, even if $\Delta$ increases during a step, subsequent steps reduce it eventually.

The shift 130a can be performed by giving a verbal command to the patient to move his/her eye, or by physically moving the patient's head, or the surgical bed the patient is resting on, or by manually moving the patient's eye, or by moving a fixation light of a fixation light source, or by moving a directing light on a directing light display, in either case directing the patient to follow the light with his eye, or by moving the docking unit 200 in an x-y plane via moving a gantry or an articulated arm. In implementations using two piece docking units, the piece which was attached to the eye, such as a gripper, can be used to move or rotate the eye. The fixation or directing light can be directed either into the surgical eye or into the non-surgical eye. These adjustments can be performed manually by the surgeon, or by operating one or more electric actuators, or by a computer. In some cases, more than one of the above types of shifts can be performed jointly.

FIG. 7 also illustrates that in other implementations the alignment-improving step 130 may include extracting orientation information regarding the lens 5 or another targeted internal structure of the eye from the generated image 122, and adjusting an orientation of at least one of the eye 1 or the docking unit 200 in relation to the extracted orientation information.

In an implementation, the surgeon can analyze the y-z image 122, generated by the imaging step 120, and determine the angle $\alpha$ between the optical axis 16 of the lens 5 and the optical axis 202 of the docking unit 200. Based on this determination, the surgeon can rotate either the eye, or the docking unit, or shift the docking unit, or adjust an optical path of the laser beam in the laser surgical system 50 to overcome this a misalignment. The option of rotating the eye is indicated by arrow 130b. This alignment-improving step 130 can reduce or even eliminate the angle $\alpha$ between the optical axis 16 of the lens 5 and the optical axis 202 of the docking unit 200. This alignment-improvement is typically achieved by introducing an angle between the optical axis 12 of the eye and the optical axis 202 of the docking unit 200, as indicated by the dotted line.

The rotation 130b may be performed iteratively because in the first try the surgeon may not have determined the angle $\alpha$ precisely. To remedy this, in some implementations the alignment-improving step 130 may be followed by a repeated imaging step 120' to determine the angle $\alpha'$ after the rotation 130b from a repeated image 122', followed by a repeated alignment-improving step 130' based on the image 122' generated by the repeated imaging step 120' and so on. In efficient implementations, the angle $\alpha$ is reduced step-by-step. In other implementations, even if $\alpha$ increases during a step, subsequent steps eventually reduce it.

The rotating step 130b can be performed by giving a verbal command to the patient to rotate his/her eye, or by manually rotating the patient's head, or by physically rotating the patient's eye, or by moving a fixation light of a fixation light source, or a directing light displayed on a display, in either case directing the patient to follow the light with his eye, or by moving or rotating the docking unit 200 in the x-y plane via moving a gantry or an articulated arm. The fixation or directing light can be directed either into the surgical eye or into the non-surgical eye. In implementations using two piece docking units, the piece which was attached to the eye, such as a gripper, can be used to move or rotate the eye. These adjustments can be performed manually by the surgeon, or by operating one or more electric actuators, or by a computer. In some case, more than one of the above types of shifts can be performed jointly.

Figure 8B:
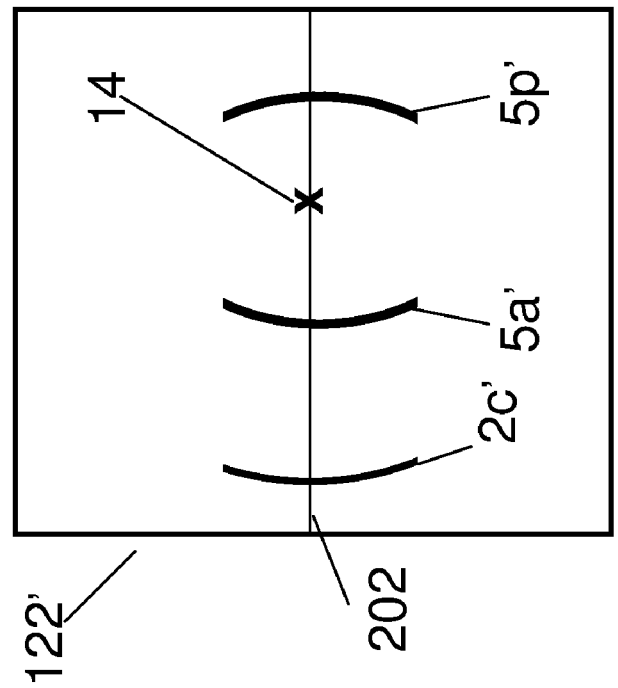
FIGS. 8A-B illustrate the alignment of the docking unit with the lens after the alignment-improving step, and the corresponding image.
Figure 8A:
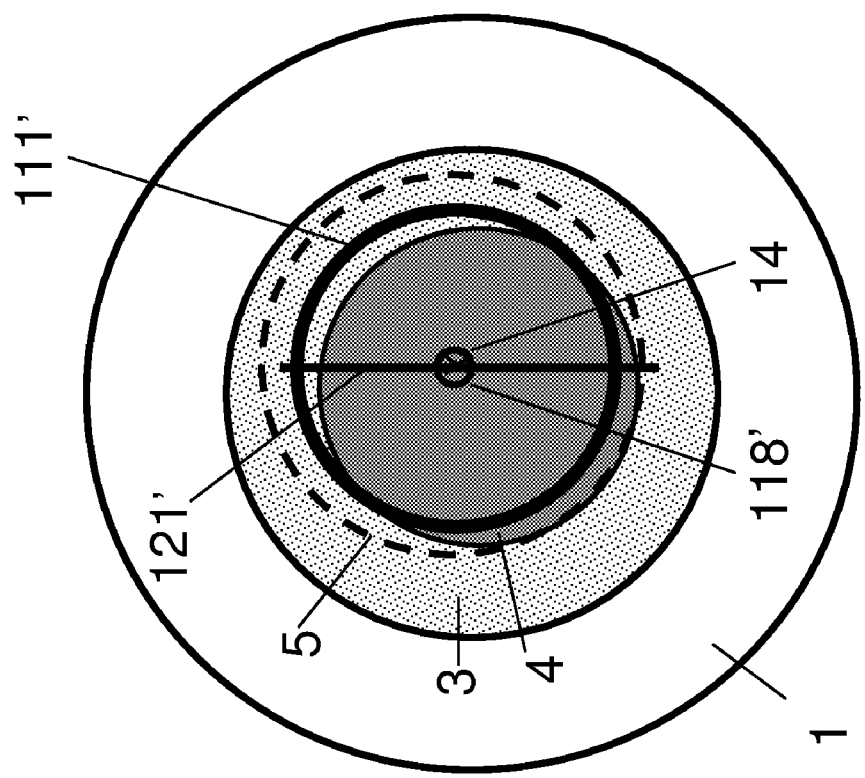

FIGS. 8A-B illustrate an outcome of the imaging step 120 and alignment-improving step 130.

FIG. 8A illustrates that after a successful alignment-improving step 130, a shifted target pattern circle 111' may have become concentric with the lens 5 instead of the pupil 4. Correspondingly, the shifted linear scanning line 121', across the shifted center 118' of the target pattern circle 111', can now go through the center 14 of the lens 5 instead of the center of the pupil 4.

Some implementations may display both the first target pattern circle 111 concentric with the pupil 4, as well as a second target pattern 111' which is shifted by the alignment-improving step 130 to be concentric with the lens 5.

FIG. 8B illustrates that after an efficient alignment-improving step 130, a repeated imaging step 120' may record a cross-sectional y-z image 122' showing that the center 14 of the lens now lies on the optical axis 202 of the docking unit 200. Further, the images of the anterior and posterior capsule segments 5a' and 5p' after the relative rotation and shift of the eye and the docking unit 200, are close to symmetric, indicating that the optical axis 16 of the lens is approximately aligned with the optical axis 202 of the docking unit 200.

Achieving alignment of the docking unit 55/200 with the hard-to-see, displaced and tilted lens 5 instead of the visible pupil 4 with such an improved precision is one of the benefits of the image-guided docking method 100.

Figure 9:
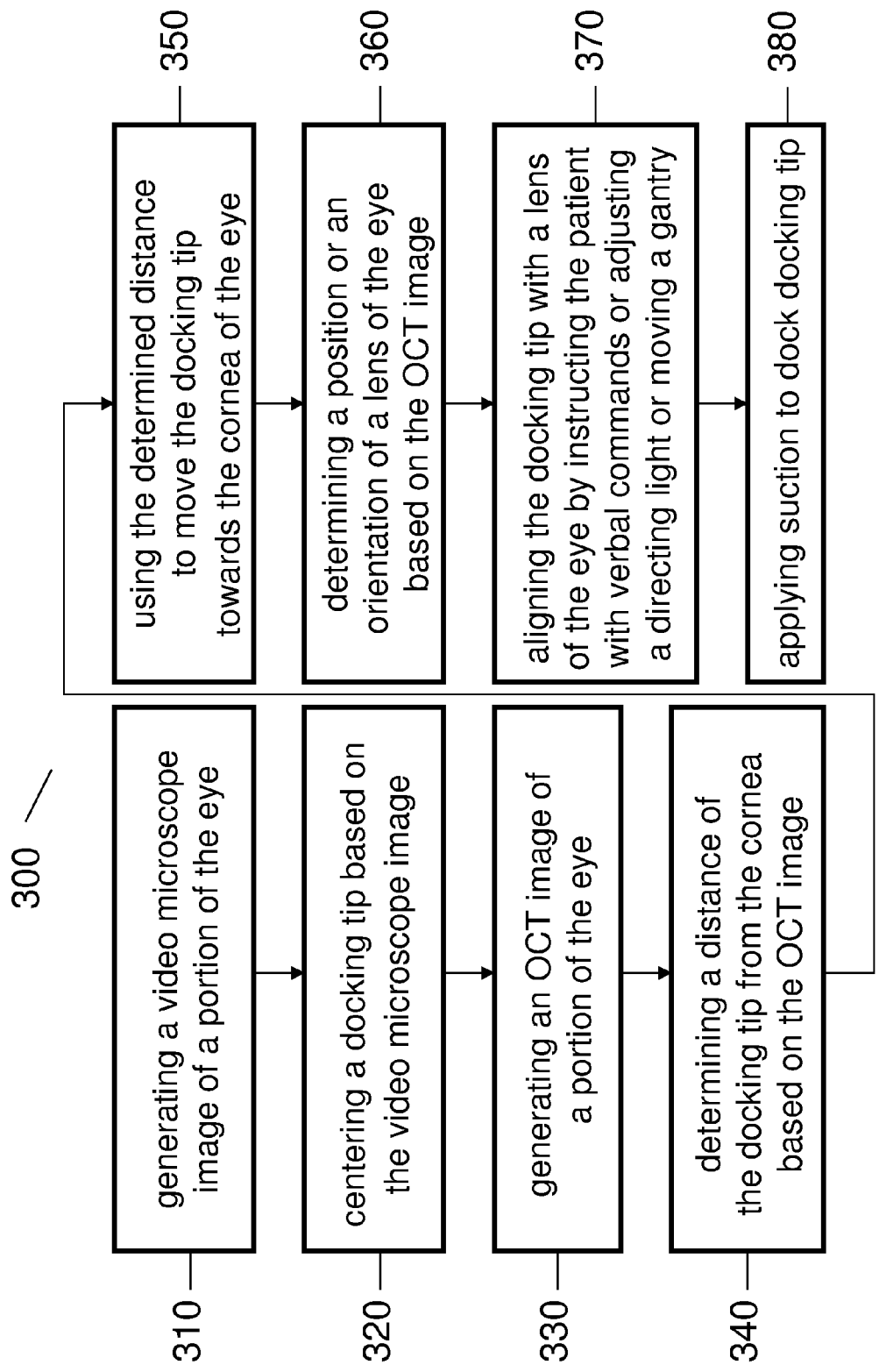
FIG. 9 illustrates a docking method guided by an imaging method.

FIG. 9 illustrates that an implementation of a related image-guided docking method 300 may include the steps of:

A video imaging step 310, for generating a video microscope image of a portion of the eye;

A centering step 320, for centering a docking tip based on the video microscope image;

An OCT imaging step 330 for generating an OCT image of a portion of the eye;

A distancing step 340 for determining a distance of the docking tip from the cornea based on the OCT image;

A moving step 350 for using the determined distance to move the docking tip towards the cornea of the eye;

A determining step 360 for determining a position or an orientation of a lens of the eye based on the OCT image;

An aligning step 370 for aligning the docking tip with a lens of the eye by instructing the patient with verbal commands, or adjusting a directing light or moving a gantry; and A docking step 380 for applying suction to dock the docking tip.

Several of the steps 310-380 of the method 300 can proceed analogously with the corresponding steps 110-140 of the method 100. In addition, the distance-determining step 340 can include determining the distance between the cornea 2 of the eye and the docking tip, which can be the docking unit 55 or 200, or any other patient interface. In this step 340, the distance from the docking tip can be based on a reference point. This reference point can be located in the optical system of the surgical laser system 50, for example in the objective 54. This reference point can be movable, and may be adjusted or offset based on various considerations.

Figure 10:
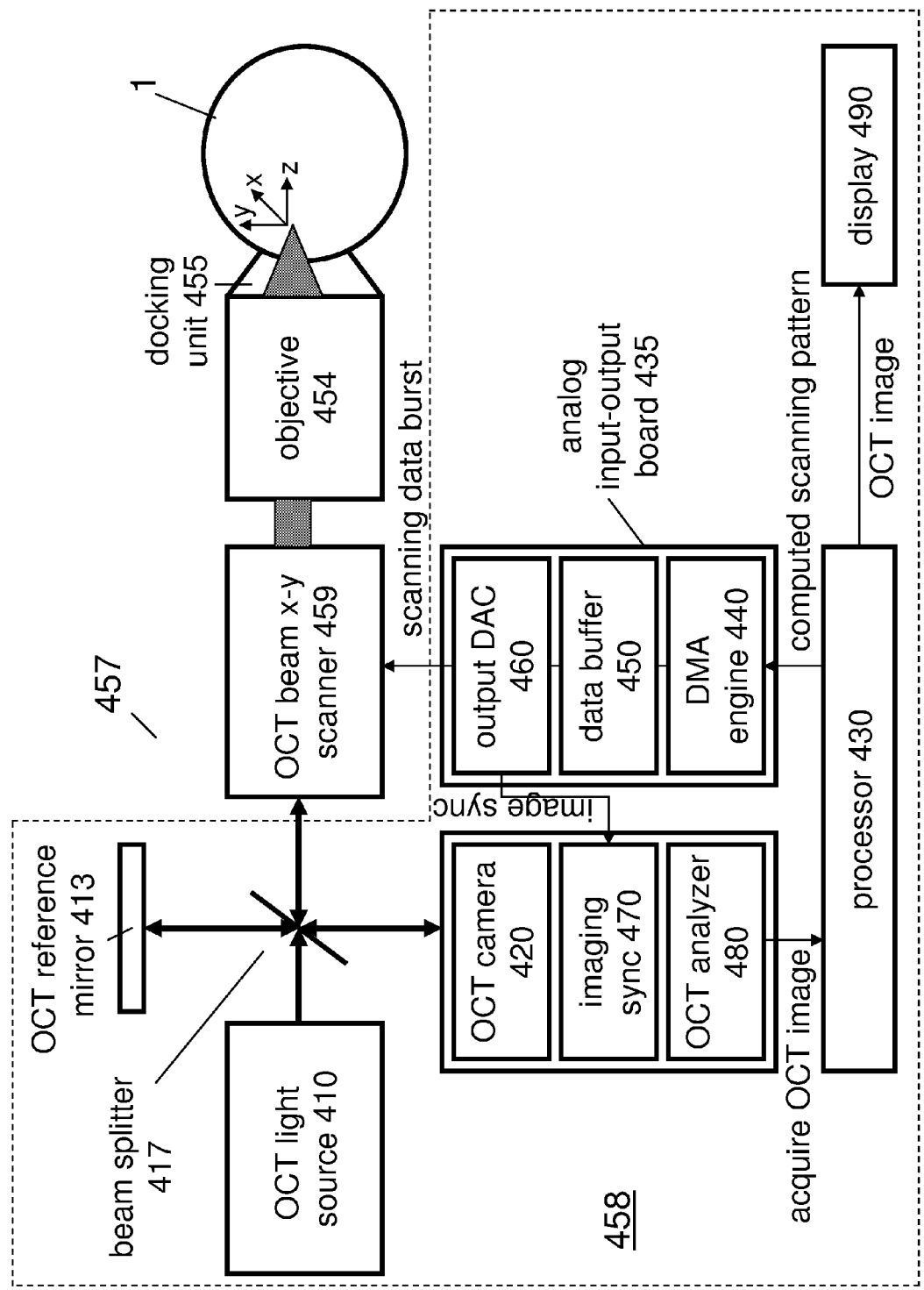
FIG. 10 illustrates an image-guided docking system.

FIG. 10 illustrates an OCT imaging system 457 to illustrate the details of the imaging step in greater detail. The OCT imaging system 457 can include an OCT imaging unit 458 and an OCT x-y scanner 459.

The principles of the operation of OCT imaging systems are well known and documented. The OCT system 457 can be a (a) time domain, a (b) swept source or a (c) spectrometer based OCT. The (a) and (b) types of OCT imaging systems use a narrow band OCT light source 410 and scan the beam's focal point in the z-direction, thus they provide imaging information corresponding to different z-depths sequentially in time. The (a) type time domain OCT systems move a reference mirror, whereas the (b) type swept source OCT systems sweep the wavelength of the laser beam.

The (c) type spectrometer based OCT systems utilize a broad band OCT imaging light source 410 and capture images from a range of z-depths essentially simultaneously, or in parallel, corresponding to the different wavelengths within the broad band of an OCT imaging light source. Because of this parallel imaging aspect, spectrometer-based OCT systems can be substantially faster that sequential OCT systems. The (b) and (c) type OCT systems are sometimes referred to as frequency domain OCT systems.

All types of OCT imaging units 458 can include an OCT light source 410, an OCT reference mirror 413 and a beam splitter 417. Among the sequential OCT systems, for the (a) type time domain OCT, the OCT light source 410 can be a narrow band laser and the reference mirror 413 movable for z-scanning. For the (b) type swept source OCT, the reference mirror need not be movable as the wavelength of the light source 410 is varied. For (c) parallel OCT systems, the OCT light source 410 can emit a broadband imaging light.

The OCT imaging beam can be guided by the OCT beam x-y scanner 459, directed to the eye via an objective 454 and a docking unit 455. The OCT x-y scanner 459 can scan the OCT imaging beam in the eye in the x and y directions. In sequential OCT systems the beam is z scanned by moving either the reference minor 413 or by sweeping the wavelength of the OCT light source 410. In parallel OCT systems, no z-scanning is performed, as the different wavelengths carry the imaging information corresponding to different z depths essentially simultaneously.

In all these system, the OCT imaging beam returned from the eye can be unified with the reference beam returning from the OCT reference mirror 413 at the beam splitter 417. This unified beam carries the imaging information in a complex interference pattern that is recorded by an OCT camera 420.

For sequential OCT systems this OCT camera 420 can be simple, e.g. including a photodetector. For parallel OCT systems the OCT imaging unit 458 may include a spectrometer, such as a prism or a grating (not shown explicitly) that resolves the broad band imaging light into its different wavelength components, and deflects the different wavelength components to different spatial angles. In some parallel OCT systems the OCT camera 420 may include a linear array of CCD detectors to capture these diverging rays with different wavelength, each carrying interference information, specific for its own wavelength. In others, a two dimensional CCD array can be used. The amplitude of the resolved diverging rays can be recorded in the individual pixels of the CCD array of the OCT camera 420. Some high resolution OCT cameras 420 can involve hundreds or even thousands of pixels.

The imaging process can by controlled by an imaging sync block 470, which may get its sync signal from a later-specified output unit. The image data from the OCT camera 420 can be forwarded to an OCT analyzer 480, synchronized by the imaging sync block 470. In parallel OCT systems the OCT analyzer 480 may include a processor to perform a Fast Fourier Transform (FFT). The FFT converts the interference information of different wavelength components into image information corresponding to different z-depths. After the FFT, the transformed OCT image data represent image information corresponding to a range of z-depths. This transformed OCT image data may be forwarded to a processor 430, which can generate an OCT image and output the generated OCT image towards a display 490.

Next, an OCT scanning-beam-controller system will be described that solves the difficulties of the operation of some existing OCT scanning-beam-controllers which are described next.

In some OCT imaging systems the processor 430 can multitask and perform more than one function in an interleaved, parallel or overlapping manner. To carry out these functions, the processor may perform an "interrupt" by switching from e.g. the task of scanning the beam to another task and back. Such interrupts, however short, can cause problems, since during the time when the scanning is stopped or frozen by the interrupt, the laser beam may remain pointed to the same position. This scanning-freeze can disrupt the timing of the x-y scan, introducing an error and noise into the coordinates of the imaged location. This timing error in the outputted scanning data can lead to delays that may reach 50, 100 or more microseconds: a phenomenon sometimes called jitter. Further, the extended exposure to the laser beam can cause damage to the sensitive eye tissue.

In addition, since the processor typically communicates with input/output agents through a system bus, this output mode only provides slow data transfer rates, since several agents may access the bus simultaneously, all demanding a fraction of its cycle time. Further, to manage these competing demands, a portion of the cycle of the system bus is typically taken up by control signals. And if an OCT imaging system is designed to avoid this scanning-freeze by the processor outputting the scanning data to an output unit in a single-task mode, e.g. through a dedicated link, then the processor cannot perform other functions during this outputting step, such as computing the next scanning pattern. All these designs and data constraints slow down the performance of such systems considerably.

Implementations of the presently described OCT scanning-beam-controller can overcome these difficulties by employing an efficient design. The OCT scanning-beam-controller can include the processor 430 and an analog input-output board 435. The processor 430 can compute scanning data for a scanning pattern. This scanning data can include e.g. a sequence of x-y coordinates where the OCT imaging beam will be directed in the target region in the course of scanning. For sequential, z-scanning OCT systems, the scanning data can include x-y-z coordinates. As described above, the OCT scanning pattern can be a wide variety of patterns, including lines, arcs, loops, circles, spirals, raster and grid patterns.

The processor 430 can compute the scanning data, as well as perform its other described functions in connection to a storage medium that stores a computer code or instruction set to facilitate these functions of the processor.

The analog input-output board 435 can include a local or dedicated memory controller 440, also referred to as a direct memory access engine 440, or DMA engine 440. The DMA engine/memory controller 440 can manage a transfer of the computed scanning data, indirectly or directly, from the processor 430 toward a data buffer 450. The data buffer 450, coupled to the local memory controller 440 can store the scanning data and output the scanning data towards an output digital-analog converter 460, or output DAC 460. The output DAC 460 can be coupled to the data buffer 450 and can (i) convert selected outputted scanning data to analog scanning signals, and (ii) output the scanning signals towards the OCT beam x-y (or x-y-z) scanner 459.

Figure 11:
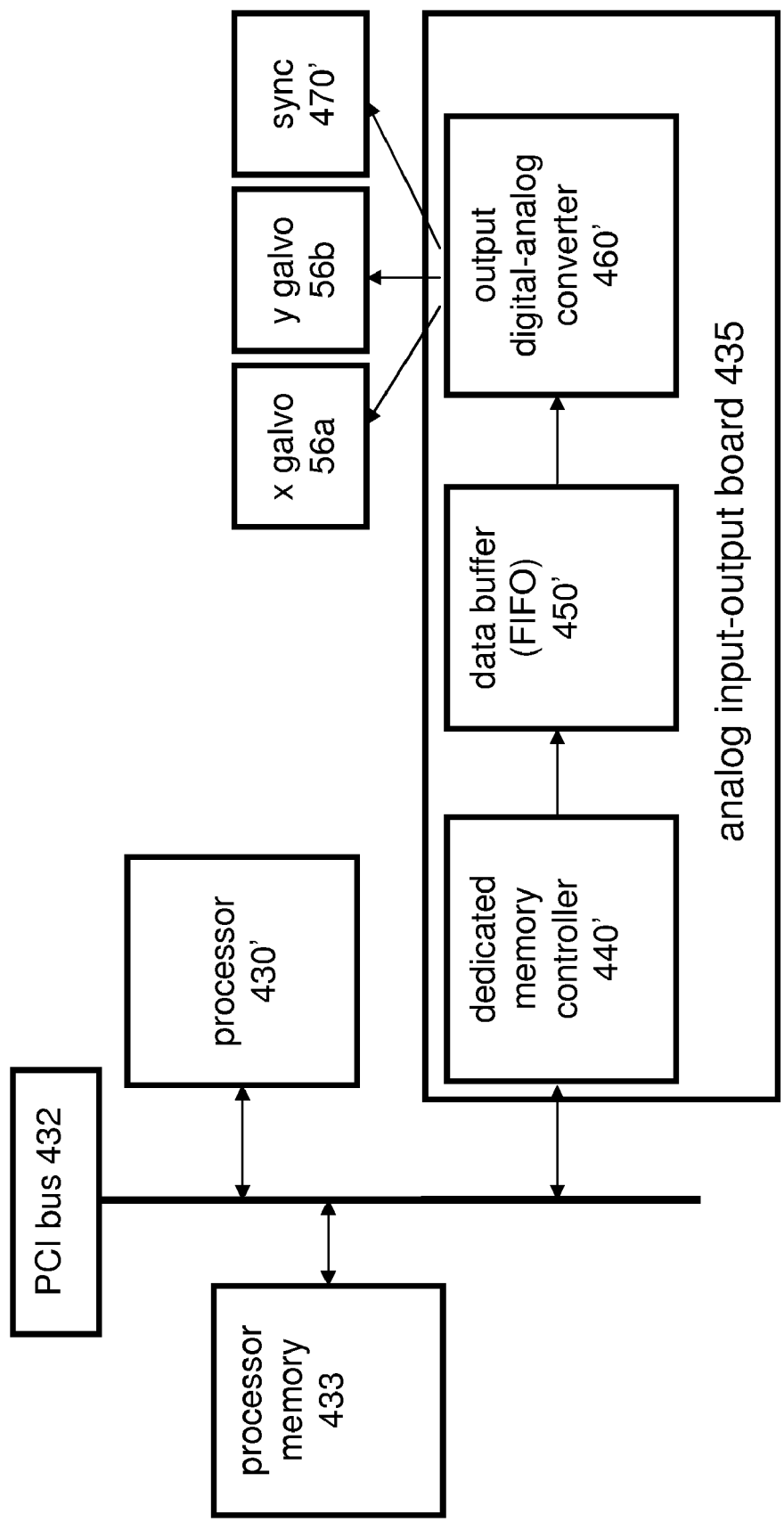
FIG. 11 illustrates blocks of the image-guided docking system in detail.

FIG. 11 illustrates an implementation of the OCT scanning beam-controller. The processor 430' can be coupled to a bus 432, such as a PCI bus 432. The OCT scanning-beam-controller can also include a processor memory 433. The processor 430' can output the computed scanning data to the processor memory 433. The dedicated DMA engine 440' can transfer the scanning data from the processor memory 433 to the data buffer 450' which can be e.g. a first-in-first-out (FIFO) memory. The FIFO buffer memory 450' can store the scanning data and output the stored scanning data to the output DAC 460' when prompted. In some implementations, the processor can output the scanning data to the analog input-output board 435 through a dedicated memory bus or local bus instead of a PCI bus 432. In other implementations, there can be even a direct connection between the processor and the DMA engine 440'.

In relation to the above described problems with other systems, embodiments of the present OCT scanning-beam-controller offer a fast scanning operation as (i) the FIFO memory 450' can output the stored scanning data in an uninterrupted manner; (ii) the output mode can be a fast data transfer mode, such as a burst mode; and (iii) the output can be performed without sending the scanning data through the shared bus 432, the processor memory 433, or the processor 430'.

For all these reasons, the outputting of the scanning data will not be interrupted by competing tasks, or slowed down by the slow data transfer characterizing the shared bus 432.

Further, since the FIFO memory 450' drives the outputting of the scanning data, the processor 430' is free to perform other functions in parallel with the data output, such as processing an image, or computing new scanning data corresponding to a scanning pattern, or performing a control function.

In addition, the output of the scanning data by the data buffer 450' to the output DAC 460' is not slowed down by an interrupt by the processor 430 or another system agent either since the output proceeds from the data buffer 450' through a dedicated channel on the analog input-output board 435 instead of the shared bus 432. Such implementations can reduce the jitter considerably, such as keeping it below 50, 40, or even 20 microseconds.

In some implementations, the output DAC 460' can convert the received digital scanning data into analog scanning signals and output the scanning signals to x and y galvo-controllers 56a and 56b, or some other types of scanning-controllers that control x and y galvo mirrors, or redirector elements, to scan the OCT imaging beam according to the scanning pattern, coded in the scanning data. Some implementations may have an integrated x-y galvo-controller that controls a minor capable of rotating around two axes.

The output DAC 460' can also output synchronizing signals to the imaging sync block 470' coupled to the OCT imaging camera 420 to record the returned OCT imaging beam synchronously with the scanning of the OCT imaging beam. The synchronizing signals can be based on synchronizing data, inserted by the processor 430' into the scanning data.

In addition, the imaging step 120 can include computing homing data corresponding to a homing pattern connecting an ending point of a first imaging step to a starting point of a subsequent second imaging step. This step can be useful in implementations where the first imaging step ends by simply stopping the output of the scanning data, thus leaving the scanning x and y galvos 56a-b in a non-standard position and the imaging beam pointed to a non-standard target point. This non-standard point is typically different from the starting point of the subsequent second imaging step, thus necessitating the "homing" of the x and y galvos 56a-b by computing and outputting homing data, so that the imaging beam can start the subsequent second imaging step from a well-defined starting point.

As an example, the first imaging step may include scanning the x and y coordinates of the imaging beam along a first circle of a first radius. If the second imaging step includes scanning along a second circle of a second radius, then the first imaging step can be followed by computing homing data that define a path from the endpoint of the first circular scan with the first radius to the starting point of the second circular scan with the second radius.

Such implementations can avoid moving the imaging beam back to a standard point, e.g. to a center, origin, or otherwise unbiased point, thus saving additional time and further accelerating the scanning operation.

The computing of the homing data can be also useful in implementations where at the end of the first imaging step the x and y galvos 56a and 56b are returned to a neutral position, as it facilitates the computing of the starting position of a second imaging step in relation to the neutral position.

In some implementations, the speed of the output of the output DAC 460/460' can be so fast that an operating speed of the imaging system 457 can be limited by an integration time of the OCT camera 420.

In some implementations, the output DAC 460/460' can output the scanning signals at a rate within one of the following ranges: 1 Hz-1 MHz, 100 Hz-1 MHz, or 1 kHz-100 kHz.

In some implementations, the rate of output for the scanning signals can be adjustable according to the requirements of the imaging task and pattern.

Once the imaging step 120 is completed, the alignment-improving step 130 can include providing a verbal command to a patient based on the image of the internal structure of the eye, such as the lens 5.

The alignment-improving step 130 can also include providing a fixation light beam, asking the patient to look at the fixation light, and adjusting the fixation light based on the image provided by the imaging step 120. The fixation light can be provided into the surgical eye, through the main optical pathway of the laser surgical system 50, or through a separate fixation light system. In some cases the fixation light can be provided to the non-surgical eye.

The alignment-improving step 130 can be started (i) before the docking unit 55/200 makes contact with the eye; (ii) after the docking unit 55/200 makes contact with the eye but before an application of a vacuum; or (iii) after an application of a partial vacuum in relation to the docking unit 55/200 that still allows some degree of alignment modification.

The partial vacuum, or suction, can be applied, for example, through a suction ring or suction skirt, which can be part of the docking unit 55/200. The suction can be applied after the eye was brought into physical contact with the eye.

The docking method 100 can be performed as part of a surgical process or a diagnostic process. In other implementations, the docking method 100 can be part of an imaging procedure, which is not part of a surgical or a diagnostic procedure, such as an identification process.

The steps 110-140 can involve program codes or instruction sets that are stored in the imaging system 57. The code can be stored e.g. in a dedicated memory or in a memory that is part of another functional block. The aligning step 110 can involve a code stored in a memory related to the video microscope 56. The imaging step 120 can involve storing the scanning patterns or scanning data generated by the processor 430 in a dedicated or integrated memory, or storing scanning data in the data buffer 450. The alignment-improving step 130 can include using a memory unit for storing the generated image to help improving the alignment of the docking unit 55 with the lens of the eye 1 in relation to the generated image. The docking step 140 can also use a stored program to guide and control the docking unit 200 docking with the eye.

Figure 12:
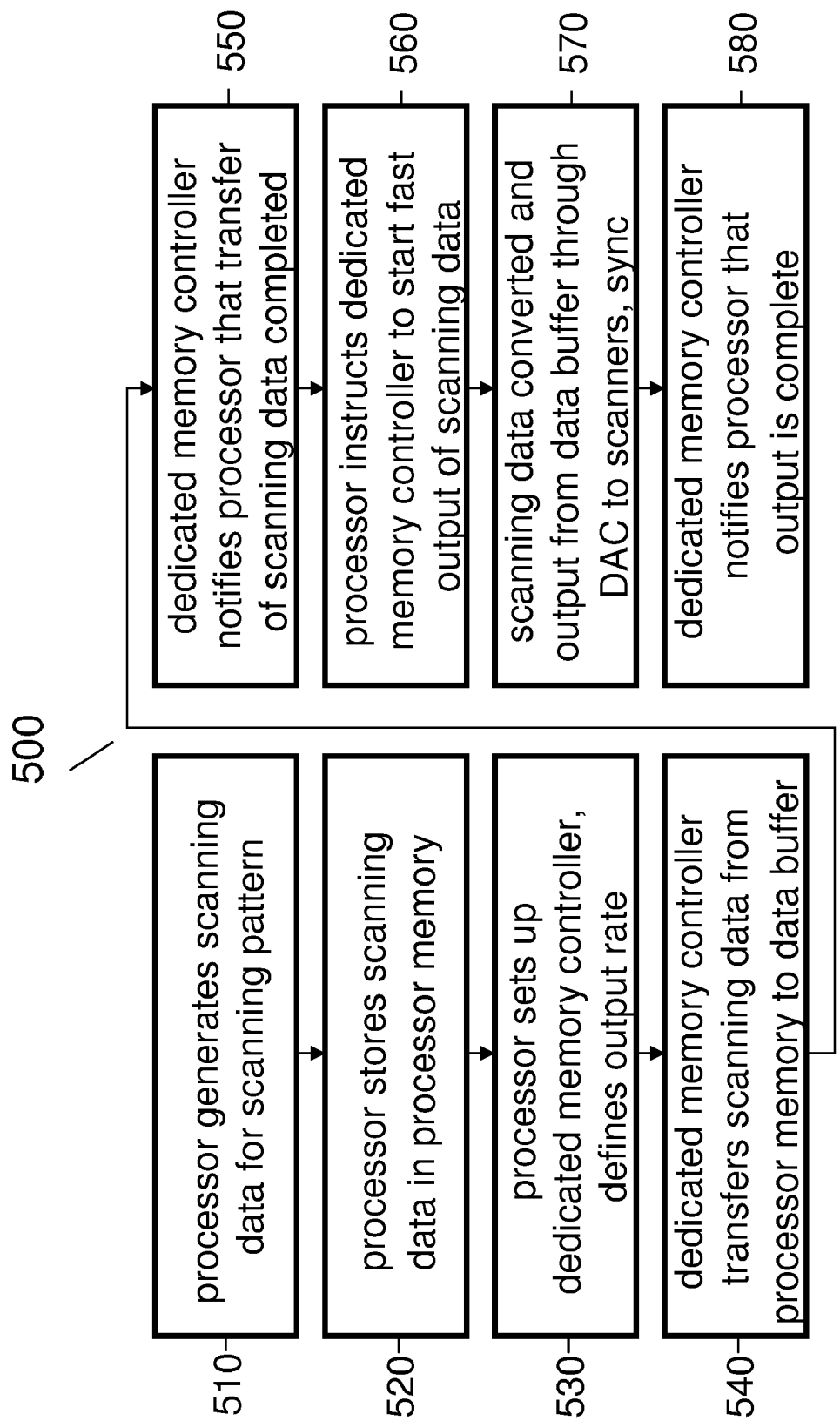
FIG. 12 illustrates the steps of a control method of the image-guided docking method.

FIG. 12 illustrates that an implementation of a fast imaging method 500 can include:

A step 510 of computing scanning control data by the processor 430/430';

A step 520 of storing the scanning control data into the processor memory 433 by the processor 430;

A step 530 of setting up the dedicated memory controller 440/440' for a scanning operation by defining operation parameters, such as a scanning output rate;

A step 540 of transferring scanning control data from the processor memory 433 to the data buffer 450/450' at least partially under the control of the dedicated memory controller 440/440';

A step 550 of notifying the processor 430/430' by the dedicated memory controller/DMA engine 440/440' that the transfer of the scanning control data has been completed;

A step 560 of instructing the dedicated memory controller 440/440' by the processor 430/430' to start fast output of the scanning control data;

A step 570 of transferring the scanning control data from the data buffer 450/450' to the output DAC 460/460' at least partially under the control of the dedicated memory controller 440/440', the output DAC 460/460' converting the digital scanning control data to analog scanning control signals, and the output DAC 460/460' outputting the analog scanning control signals to the x and y scanners 56a and 56b, and to the sync block 470;

A step 580 of notifying the processor 430/430' by the dedicated memory controller 440/440' that the output process is complete.

In the step 570, the transferring the scanning control data from the data buffer 450/450' can be performed in a fast transfer mode, such as a burst mode, or a page mode, or any similarly fast transfer modes.

In the step 570, the transferring of the scanning control data from the data buffer 450/450' can be performed without sending the scanning control data through the bus 432 that connects the local memory controller 440, the processor 430, and the processor memory 433.

In the step 570, the transferring step can also include transferring the scanning control data in parallel with the processor 430 processing an image or computing scanning data corresponding to a scanning pattern.

In the step 570, the transferring step can also include transferring the scanning data without an interrupt by another system agent, thereby keeping a jitter of the scanning data below 50, 40, or 20 microseconds.

In an implementation 600 of the above method 500, the above steps can be organized into the following steps:

A step 610 of computing scanning control data by a processor can include the step 510;

A step 620 of storing the scanning control data into a data buffer partially by a local memory controller can include the steps 520, 530, 540, and 550;

A step 630 of transferring the scanning control data from the data buffer in a fast transfer mode to a converter-output module can include the steps 560 and elements of the step 570; and A step 640 of outputting scanning signals to scanning controllers, the scanning signals converted from the scanning control data by the converter-output module can include elements of the step 570.

While this specification contains many specifics, these should not be construed as limitations on the scope of any invention or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The invention claimed is:

1. A docking method for an ophthalmic system, the method comprising:

aligning a docking unit of the ophthalmic system and an eye;

generating an image of an internal structure of the eye by an optical coherence tomographic imaging system after aligning the docking unit and the eye;

improving an alignment of the docking unit with the internal structure of the eye in relation to the generated image; and docking the docking unit to the eye with the improved alignment the generating the image step comprising:

computing scanning data by a processor corresponding to a scanning pattern;

storing the scanning data in a dedicated data buffer;

transferring the scanning data by the dedicated data buffer to an output module partially under the control of a dedicated memory controller;

outputting scanning signals by the output module to one or more scanners based on the scanning data; and scanning an imaging beam with the one or more scampers according to the scanning signals.

2. The method of claim 1, the aligning the docking unit step comprising:

using a first imaging system to align a target pattern of the ophthalmic system in relation to a feature of the eye.

3. The method of claim 2, wherein:

the first imaging system is one of a microscope or a video microscope;

the target pattern of the ophthalmic system includes at least one of a center of a contact lens, a center of the docking unit, a docking circle, or a docking cross-hair; and the feature of the eye is at least one of a center of a region of an iris, a pupil, a cornea, a limbus, or a lens; or a circular formation related to a region of the iris, the pupil, the cornea, the limbus or the lens.

4. The method of claim 1, the improving an alignment step comprising:

extracting position information regarding the internal structure of the eye from the generated image; and adjusting a position of at least one of the eye or the docking unit in relation to the extracted position information.

5. The method of claim 1, the improving an alignment step comprising:

extracting orientation information regarding the internal structure of the eye from the generated image; and adjusting an orientation of at least one of the eye or the docking unit in relation to the extracted orientation information.

6. The method of claim 1, the computing the scanning data step comprising:

implementing a scanning pattern that includes at least one of a linear pattern, a circular pattern, an oval pattern, a loop pattern, an arc pattern, a raster pattern, an x-y pattern, a crosshair pattern, a star pattern, a spiral pattern, and a pattern with outlying points.

7. The method of claim 1, the computing the scanning data step comprising:

including synchronizing signals into the scanning data by the processor.

8. The method of claim 1, the computing the scanning data step comprising:

computing homing data corresponding to a homing pattern connecting a starting point of the scanning pattern to a previously set point.

9. The method of claim 1, the storing the scanning data step comprising:

storing the scanning data in a processor memory; and transferring the stored scanning data from the processor memory to the dedicated data buffer partially under the control of the dedicated memory controller.

10. The method of claim 9, wherein:

the dedicated memory controller comprises a direct memory access engine; and the dedicated data buffer comprises a first-in-first-out memory.

11. The method of claim 1, the transferring the scanning data step comprising:

outputting the scanning data by the dedicated data buffer to the output module in a fast data transfer mode.

12. The method of claim 1, the transferring the scanning data step comprising:

outputting the scanning data from the dedicated data buffer without sending the scanning data through at least one of a bus connecting the dedicated memory controller and the processor, the processor memory, or the processor.

13. The method of claim 1, the transferring the seaming data step comprising:

outputting the scanning data in parallel with the processor performing at least one of processing an image, computing scanning data corresponding to a scanning pattern, or performing a control function.

14. The method of claim 1, the transferring the scanning data step comprising:

receiving the scanning data by the output module without an interrupt by another system agent, thereby keeping a jitter of the scanning data below 40 microseconds.

15. The method of claim 1, the outputting the scanning signals step comprising:

converting the scanning data into analog scanning signals by the output module, wherein the output module includes a digital-analog converter.

16. The method of claim 1, the scanning an imaging beam step comprising:

receiving the outputted scanning signals by a scanning controller and an imaging synchronizer, wherein the scanning signals comprise synchronizing signals;

repeatedly adjusting the one or more scanners by the scanning controller according to the scanning signals to scan the imaging beam; and repeatedly synchronizing an imaging camera by the imaging synchronizer according to the synchronizing signals.

17. The method of claim 16, wherein:

the scanning controller comprises at least one galvo-controller; and the imaging synchronizer comprises at least one ophthalmic coherence imaging camera controller.

18. The method of claim 1, wherein:

an integration time of an image recording device is a limiting factor of an operating speed of an imaging system.

19. The method of claim 1, the outputting the scanning signals step comprising:

outputting the scanning signals at a rate within one of the following ranges:

1 Hz-1 MHz, 100 Hz-1 MHz, or 1 kHz-100 kHz.

20. The method of claim 1, the outputting the scanning signals step comprising:
adjusting an output rate of the output of the scanning signals.

21. The method of claim 1, the improving the alignment step comprising at least one of:
providing a verbal command to a patient to move his eye,
moving the patient's head,
moving a surgical bed the patient is resting on,
moving the patient's eye,
moving the docking unit via moving a gantry or an articulated arm, and
using a gripper to move the eye,
based on the image of the internal structure of the eye.

22. The method of claim 1, the improving the alignment step comprising:
adjusting at least one of a fixation beam or a directing light to improve the alignment of the eye and the docking unit; and
directing the patient to follow the fixation beam or the directing light with his eye.

23. The method of claim 1, the improving the alignment step comprising:
starting the improving the alignment step
before the docking unit makes contact with the eye,
after the docking unit makes contact with the eye but before an application of a partial vacuum to the docking unit, or
after an application of a partial vacuum.

24. The method of claim 1, the docking step comprising:
sensing a distance between a reference point of the docking unit and an outer layer of the eye; and
lowering the docking unit according to the sensed distance.

25. The method of claim 24, wherein:
the reference point is adjustable.

26. The method of claim 1, the docking step comprising:
bringing the docking unit into physical contact with the eye; and
applying suction through a portion of the docking unit after the docking unit makes physical contact with the eye.

27. An imaging controller for an ophthalmic system, comprising:
a processor that computes scanning data for a scanning pattern of an optical coherence tomographic imaging system;
a local memory controller that partially manages a transfer of the computed scanning data from the processor to a dedicated data buffer, wherein
the dedicated data buffer is configured to store the scanning data and to output the scanning data; and
an output digital-analog converter, coupled to the dedicated data buffer that converts selected scanning data to analog scanning signals and outputs the scanning signals to the optical coherence tomographic imaging system.

28. The imaging controller of claim 27, the local memory controller comprising:
a direct memory access engine.

29. The imaging controller of claim 27, the dedicated data buffer comprising:
a first-in-first-out memory that outputs the stored scanning data in a fast data transfer mode.

30. The imaging controller of claim 27, further comprising:
a processor memory; and
a bus, coupled to the processor, the local memory controller and the processor memory, Wherein
the processor is configured to output the computed scanning data to the processor memory through the bus; and
the local memory controller is configured to transfer the scanning data from the processor memory to the dedicated data buffer through the bus.

31. The imaging controller of claim 30, wherein:
the dedicated data buffer is configured to output the scanning data without sending the scanning data through at least one of
the bus, the processor memory, or the processor.

32. The imaging controller of claim 27, wherein:
the processor is configured to perform at least one of processing an image and computing scanning data,
while the dedicated data buffer outputs the scanning data.

33. The imaging controller of claim 27, wherein:
the output digital-analog converter is coupled to the dedicated data buffer so that the scanning data, outputted by the dedicated data buffer is received without an interrupt by another system agent,
thereby keeping a jitter of the scanning data below 40 microseconds.

34. The imaging controller of claim 27, wherein:
the output digital-analog converter is configured to output the scanning signals to x and y scanning controllers to scan an imaging beam; and
synchronizing signals to an imaging camera to record a returned imaging beam synchronously with the scanning.

35. A method of controlling an ophthalmic imaging, the method comprising the steps of:
computing scanning control data by a processor for an optical coherence tomographic imaging system;
storing the scanning control data into a dedicated data buffer partially under the control of a memory controller;
transferring the scanning control data from the dedicated data buffer to a signal converter through a dedicated channel; and
sending scanning signals to a scanning controller by an output module, wherein
the scanning signals are converted from the scanning control data by the signal converter.

36. The method of claim 35, the storing the scanning control data step comprising:
storing the computed scanning control data in a processor memory; and
moving the scanning control data from the processor memory to the dedicated data buffer.

37. The method of claim 36, the transferring the scanning control data step comprising:
transferring the scanning data from the dedicated data buffer without sending the scanning data through at least one of
a bus connecting the local memory controller and the processor,
the processor memory, or
the processor.

38. The method of claim 35, the transferring the scanning control data step comprising:
transferring the scanning data in parallel with the processor performing at least one of:
processing an image; and computing scanning data corresponding to a scanning pattern.

39. The method of claim 35, the transferring the scanning control data step comprising:
  transferring the scanning data without an interrupt by another system agent,
    thereby keeping a jitter of the scanning data below 40 microseconds.

40. The method of claim 35, wherein:
  the local memory controller includes a direct memory access engine; and
  the dedicated data buffer is a first-in-first-out memory.

* * * * *